(12) United States Patent
Forsell

(10) Patent No.: US 6,482,145 B1
(45) Date of Patent: *Nov. 19, 2002

(54) HYDRAULIC ANAL INCONTINENCE TREATMENT

(75) Inventor: Peter Forsell, Menzingen (CH)

(73) Assignee: Obtech Medical AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/503,483

(22) Filed: Feb. 14, 2000

(51) Int. Cl.⁷ .................................................. A61F 2/02
(52) U.S. Cl. ........................................................ 600/30
(58) Field of Search ................................. 128/897–899; 600/29–32, 37, 593; 604/27–28; 606/139–141, 151, 157, 201–203, 213, 228; 607/41

(56) References Cited

U.S. PATENT DOCUMENTS

| | | | | |
|---|---|---|---|---|
| 3,750,194 A | * | 8/1973 | Summers | 600/31 X |
| 3,875,928 A | * | 4/1975 | Angelchik | 600/37 |
| 4,246,893 A | * | 1/1981 | Berson | 128/898 |
| 4,592,355 A | * | 6/1986 | Antebi | 606/144 |
| 4,696,288 A | * | 9/1987 | Kuzmak et al. | 128/898 |
| 5,074,868 A | * | 12/1991 | Kuzmak | 606/157 |
| 5,160,338 A | * | 11/1992 | Vincent | 606/157 |
| 5,226,429 A | * | 7/1993 | Kuzmak | 128/898 |
| 5,449,368 A | * | 9/1995 | Kuzmak | 606/157 |
| 5,509,888 A | * | 4/1996 | Miller | 600/29 |
| 5,704,893 A | * | 1/1998 | Timm | 600/29 |
| 5,769,877 A | * | 6/1998 | Barreras | 607/61 |
| 5,910,149 A | * | 6/1999 | Kuzmak | 606/157 |
| 5,938,669 A | * | 8/1999 | Klaiber et al. | 606/157 |
| 5,978,712 A | * | 11/1999 | Suda et al. | 607/41 |
| 6,074,341 A | * | 6/2000 | Anderson et al. | 600/29 |

FOREIGN PATENT DOCUMENTS

FR       2797181       2/2001

* cited by examiner

Primary Examiner—Kevin Shaver
Assistant Examiner—Joseph A. Cadugan
(74) Attorney, Agent, or Firm—Nixon & Vanderhye, P.C.

(57) ABSTRACT

An anal incontinence treatment apparatus and method includes and uses an adjustable restriction device implanted in a patient, who suffers from anal incontinence. The restriction device engages the rectum of the patient to restrict the fecal passageway. An adjustment device is adapted to adjust the restriction device such that the rectum is temporarily released, in order to open the fecal passageway when the patient wishes to achieve defaecation.

127 Claims, 12 Drawing Sheets

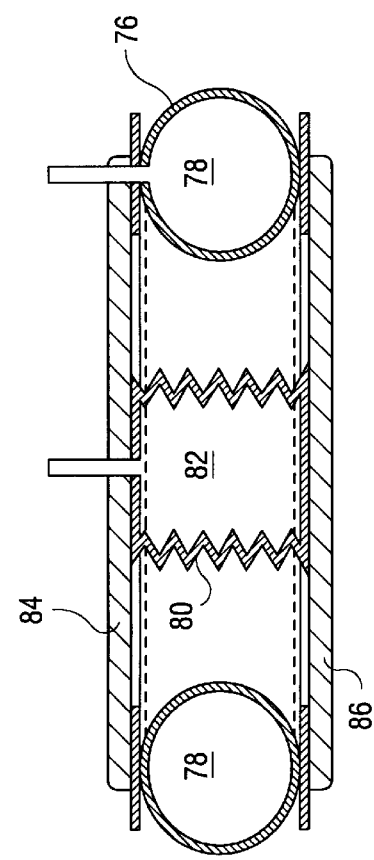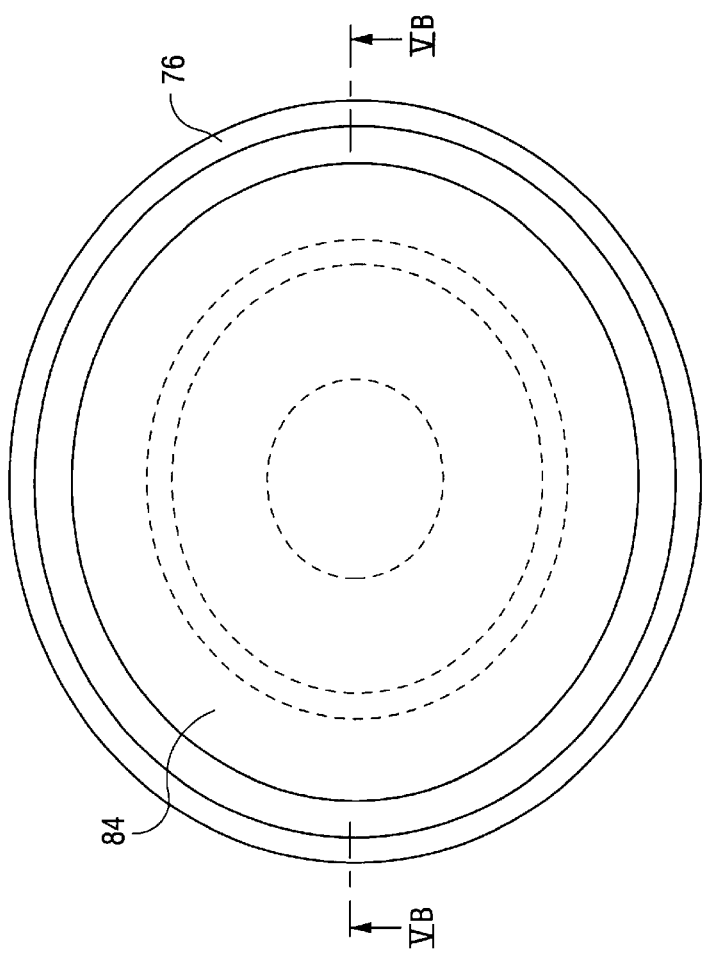
Fig. 5B
Fig. 5A

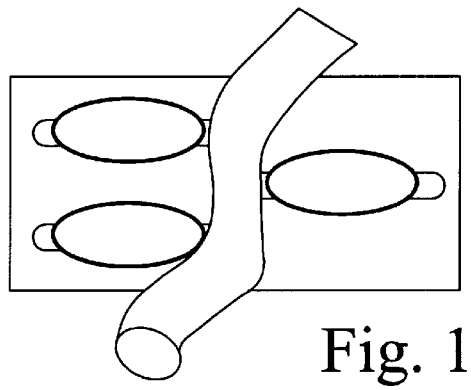 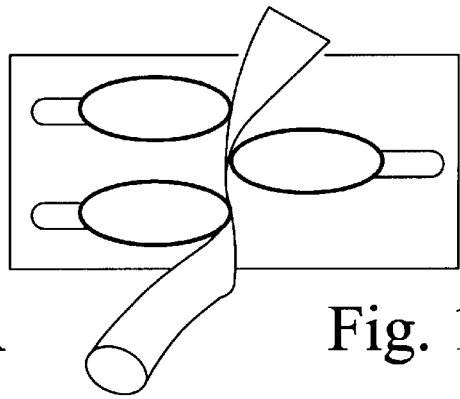
Fig. 13A				Fig. 13B
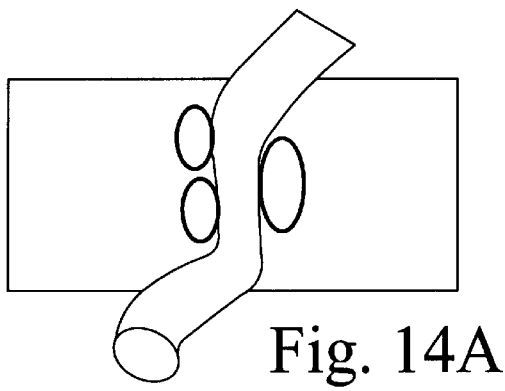 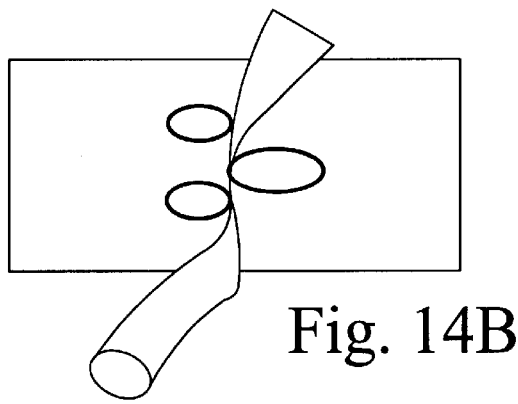
Fig. 14A				Fig. 14B
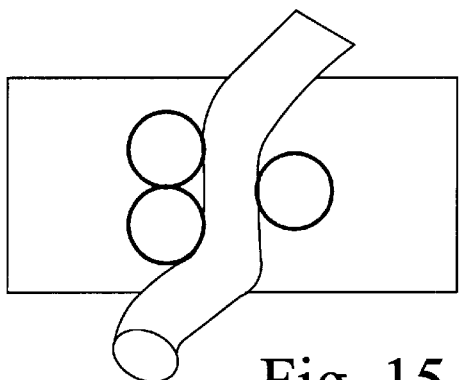 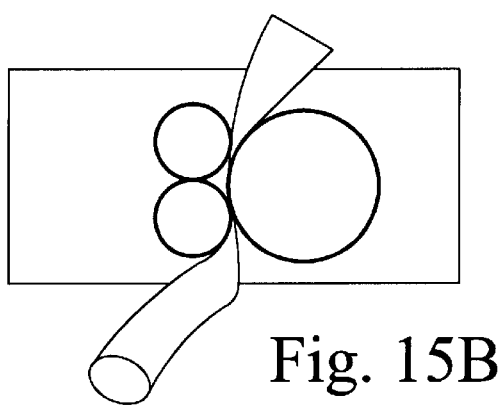
Fig. 15A				Fig. 15B

HYDRAULIC ANAL INCONTINENCE TREATMENT

BACKGROUND OF THE INVENTION

The present invention relates to an anal incontinence treatment apparatus and method. More specifically, the invention relates to an anal incontinence treatment apparatus and method for surgical application in the body of an anal incontinence patient for restricting the colon or rectum of a patient.

Anal incontinence is a widespread problem. Many different solutions to this problem have been tried. Several kinds of sphincter plastic surgery are used today to remedy anal incontinence. There is a prior manually operated sphincter system in an initial clinical trial phase with the hydraulic sphincter system connected to a reservoir placed in the scrotum. Disadvantage of this system is that hard fibrosis created around the reservoir over time may cause malfunction of pumping components. Thus, the created fibrosis will sooner or later become a hard fibrotic layer which may make it difficult to pump the reservoir. Yet a further disadvantage is that the use of hydraulic fluid always entails a risk of fluid leaking from the prosthetis. Furthermore, it is a rather complicated task to mechanically manually pump the reservoir when defaecation is needed. U.S. Pat. No. 5,593,443 discloses hydraulic anal sphincter under both reflex and voluntary control. An inflatable artificial sphincter with the pump system in scrotum is disclosed in U.S. Pat. No. 4,222,377.

SUMMARY OF THE INVENTION

A prime object of the present invention is to provide an anal incontinence treatment apparatus, which does not require manual manipulation of a combined reservoir a pump mechanism placed in the scrotum or labia majora region of the patient.

Another object of the invention is to provide an anal incontinence treatment apparatus, which does not require complicated surgery.

Yet another object of the invention is to provide an anal incontinence treatment apparatus, which may be conveniently remotely controlled by the patient.

Accordingly, the present invention provides an anal incontinence treatment apparatus, comprising an adjustable restriction device implanted in a patient, who suffers from anal incontinence, and engaging a portion of the colon or rectum of the patient to restrict the fecal passageway therein, an adjustment device which adjusts the restriction device to restrict the colon or rectum to close the fecal passageway, or release the colon or rectum to open the fecal passageway, and a powered hydraulic operation device for adjusting the adjustment device.

Preferably the hydraulic operation device adjusts the adjustment device in a non-manual manner. The expression "non-manually manner" should be understood to mean that the restriction device is not adjusted by manually touching subcutaneously implanted components of the apparatus or not manipulated by touching the skin of the patient. Preferably, the adjustment device adjusts the restriction device in a non-invasive manner. The expression powered should be understood as energised with everything without manual force, preferable electric energy.

The adjustment device may adjust the restriction device in a non-magnetic manner, i.e. magnetic forces may not be involved when adjusting the restriction device.

The adjustment device may also adjust the restriction device in a non-thermal manner, i.e. thermal energy may not be involved when adjusting the restriction device. Furthermore, as opposed to prior art anal incontinence treatment devices the adjustment device of the invention is not operated by manual forces, such as by manually compressing a fluid containing balloon implanted in the scrotum. Instead the apparatus of the invention may further comprise a powered operation device for operating the adjustment device.

In the various embodiments hereinafter described the restriction device generally forms an at least substantially closed loop. However, the restriction device may take a variety of different shapes, such as the shape of a square, rectangle or ellipse. The substantially closed loop could for example be totally flat, i.e. thin as seen in the radial direction. The shape of restriction device may also be changed during use, by rotation or movements of the restriction device in any direction.

Preferably the restriction device controls the size of the area of the fecal passageway in the colon or rectum, preferably to change steplessly with a preselected size that is satisfactory for the patient.

A control device for controlling the restriction device may conveniently be provided and may comprise an internal programmable control unit implanted in the patient and, possibly an external control unit outside the patient's body for programming the programmable internal control unit. Alternatively, the external control unit may be programmable and wirelessly control the restriction device.

At least one sensor for sensing at least one physical parameter of the patient may conveniently be implanted in the patient. The sensor preferably senses the pressure against the restriction device or the colon or rectum or other important parameters and either the internal control unit or the external control unit of the control device may suitably control the restriction device to release the fecal passage way. For safety the restrictor device may release the fecal passageway in response to the sensor sensing for example an abnormally high pressure value. The internal control unit may directly controls the restriction device in response to signals by the sensor.

The apparatus preferably comprises a control device which may comprise both an internal or an external control unit for controlling the restriction device preferable for wirelessly controlling the restriction device. Preferable the implanted internal control unit being programmable by the external control unit. The external control unit may also be programmable.

Preferably, a hydraulic operation device, suitably electrically powered, is implanted in the patient for operating the adjustment device and a reservoir is also implanted in the patient and contains a predetermined amount of hydraulic fluid, wherein the hydraulic operation device operates the adjustment device by using the hydraulic fluid of the reservoir.

In accordance with a first main embodiment of the invention, the adjustment device comprises an expandable cavity in the restriction device, the colon or rectum being sqeezed upon expansion of the cavity and released upon contraction of the cavity, and the hydraulic operation device distributes hydraulic fluid from the reservoir to expand the cavity, and distributes hydraulic fluid from the cavity to the reservoir to contract the cavity.

A fluid distribution tube may readily be connected between the reservoir and the cavity in a manner so that the tube does not interfere with other implanted components of the apparatus.

Preferably, the reservoir defines a chamber for the predetermined amount of fluid and the hydraulic operation device changes the size of the chamber. The hydraulic operation device suitably comprises first and second wall portions of the reservoir, which are displaceable relative to each other to change the size of the chamber of the reservoir. The hydraulic operation device may distribute fluid from the reservoir to the cavity of the restriction member in response to a predetermined first displacement of the first wall portion of the reservoir relative to the second wall portion of the reservoir and may distribute fluid from the cavity to the reservoir in response to a predetermined second displacement of the first wall portion relative to the second wall portion.

The first and second wall portions of the reservoir may be displaceable relative to each other by manual manipulation, such as by manually pushing, pulling or rotating any of the wall portions in one direction, or alternatively, may be displaceable relative to each other by a device powered magnetically, hydraulically, or electrically (e.g. by an electric motor). In this embodiment no pump is used, only the volume of the reservoir is varied. This is of great advantage compared to the solution described below when a pump is used to pump fluid between the reservoir and the adjustment device because there is no need for a non-return valve and it is still possible to have fluid going both to and from the reservoir.

The operation device may comprise a fluid conduit, which is devoid of any non-return valve between the pump and the cavity (including the same) and the reservoir may form part of the conduit and a fluid chamber with a variable volume. The pump may distribute fluid from the chamber to the cavity by reduction of the volume of the chamber and withdraw fluid from the cavity by expansion of the volume of the chamber. The operation device preferably comprises a motor for driving the pump, which may comprise a movable wall of the reservoir for changing the volume of the chamber. Any kind of motor could be used for the different operations as well as wireless remote solutions.

In accordance with a particular embodiment of the invention, the hydraulic operation device comprises a pump for pumping fluid between the reservoir and the cavity of the restriction device. The pump preferably comprises a first activation member for activating the pump to pump fluid from the reservoir to the cavity of the restriction device, and a second activation member for activating the pump to pump fluid from the cavity to the reservoir. The first and second activation members may be operable by manual manipulation thereof, such as by manually pushing, pulling or rotating any of the activation members in one direction. At least one of the activation members is constructed to operate when subjected to an external pressure exceeding a predetermined magnitude.

As an alternative to the manual manipulation, at least one of the first and second activating members may be operable by a device powered magnetically, hydraulically, or electrically (e.g. by an electric motor). The pump may pump fluid both to and away from the adjustment device or hydraulic device controlling the adjustment device. A mechanical solution is proposed in which it is possible to pump in both directions just by pushing an activating member in one direction. Another alternative is a pump pumping in only one direction and an adjustable valve to change the direction of fluid to either increase or decrease the amount of fluid in the reservoir. This valve may be manipulated either manually, mechanically, magnetically, or hydraulically.

Wherever a magnetic means is utilized according to the invention it may comprise a permanent magnet and a magnetic material reed switch, or other suitable known or conventional magnetic devices.

A physical lumen, like the colon or rectum or the prolongation thereof, is often easier to restrict by contracting at least two opposite or different side walls of the lumen against each other. The expression "colon or rectum or the prolongation thereof" should be understood to mean the rectum extended all the way out to the anal sphincter and following the passage of the large bowel in the other direction. It is also possible to use only one element and squeeze against human bone or tissue.

Either mechanical or hydraulic solutions may be employed to operate the restriction device. Alternatively, the restriction device may comprise an adjustable cuff, a clamp or a roller for bending the colon or rectum or the prolongation thereof to restrict the fecal passageway therein. Such a cuff, clamp or roller may also be utilized for squeezing the colon or rectum or the prolongation thereof against human material inside the body of the patient for an example the sacral bone of the patient.

Advantageously, the forming means may form the restriction member into a loop having a predetermined size.

The adjustment device may change the size of the restriction opening such that the outer circumferential confinement surface of the restriction member either is changed or is unchanged.

Preferable the restriction device comprises an elongated restriction member and forming means for forming the restriction member into at least a substantially closed loop around the colon or rectum or it's prolongation, the loop defining a restriction opening, whereby the adjustment device adjusts the restriction member in the loop to change the size of the restriction opening.

The elongated restriction member may be flexible, for example take the shape of a belt or a cord, and the adjustment device may pull a first portion of the flexible restriction member from a second portion of the flexible restriction member opposite the first portion in the loop to squeeze the colon or rectum or the prolongation thereof between two opposite lengths of the elongated flexible restriction member to restrict the fecal passageway. The restriction member may be non-inflatable, and the adjustment device may mecanically adjust the restriction member in the loop.

In accordance with a particular embodiment of the invention, the adjustment device mechanically adjusts the restriction device. Thus, the restriction device may comprise two or more elements on different sides of the colon or rectum, and the adjustment device may squeeze the colon or rectum or the prolongation thereof between the elements to restrict the fecal passageway.

In accordance with an alternative, the restriction device may comprise two articulated clamping elements positioned on opposite sides of the colon or rectum or the prolongation thereof, and the adjustment device may move the clamping elements towards each other to clamp the rectum between the clamping elements to restrict the fecal passageway.

In accordance with another alternative, the restriction device may bend the colon or rectum or the prolongation thereof. For example, the restriction device may comprise at least two bending members, such as cylindrical or hour-glass shaped rollers, positioned on opposite sides of the colon or rectum or the prolongation thereof, and the adjustment device may move the bending members against the esophagus or stomach to bend the latter to decrease the the colon or rectum or the prolongation thereof in two opposite spaced apart directions to bend the colon or rectum or the prolongation thereof to restrict the fecal passageway. The bending or rotating members may have any shape or form and be either hydralic or non-inflatable.

In accordance with another particular embodiment of the invention, the hydraulic operation device comprises a servo means, suitably including hydraulic means. Alternatively, the servo means may include magnetic or electric means. Preferably, the servo means comprises a servo reservoir defining a chamber containing servo fluid and the hydraulic operation device comprises first and second wall portions of the servo reservoir, which are displaceable relative to each other to change the size of the chamber of the servo reservoir. The same principle will apply for the servo reservoir as for the earlier described reservoir wherein the volume in the servo reservoir may be increased or decreased by a first or second displacement of the first wall portion relative to the second wall portion of the servo reservoir and thereby control the earlier described reservoir and thereby indirectly control the fecal passageway. The first and second wall portions of the servo reservoir may be displaceable relative to each other by manual manipulation, such as by manually pushing, pulling or rotating any of the wall portions of the servo reservoir in one direction. Alternatively, the first and second wall portions may be displaceable by magnetically, hydraulically or electrically powered devices. These powered devices may all be activated by manual manipulating means preferably located subcutaneously. This activation may be indirect, for example via a switch.

Especially when manual manipulation means are used, the servo means is suitable to use. With servo means less force is needed for controlling the adjustment device. Hydraulic operation is preferably used with the servo means. One example is a closed system that controls another closed system in which hydraulic components of the adjusment device are incorporated. Minor changes in the amount of fluid in a reservoir of the first system could then lead to major changes in the amount of fluid in a reservoir in the second system. Consequently, the change in volume in the reservoir of the second system affects the hydraulic operation of the adjustment device which is incorporated in the second closed system. The great advantage of such a servo means is that the larger volume system could be placed at a suitable location, e.g. inside the abdomen where there is more space, and still it would be possible to use manual manipulation means of the smaller system subcutaneously. The servo reservoir could control the reservoir of the larger volume.

The servo reservoir could be controlled directly or indirectly by a small fluid supply reservoir, which may be placed subcutaneously and may be activated by manual manipulation means controlling the servo reservoir or other suitable device.

Preferably, the hydraulic operation device comprises first and second wall portions of the fluid supply reservoir, which are displaceable relative to each other to change the size of the chamber of the fluid supply reservoir. The hydraulic operation device may distribute fluid from the fluid supply reservoir to the servo reservoir in response to a predetermined first displacement of the first wall portion of the fluid supply reservoir relative to the second wall portion of the fluid supply reservoir and to distribute fluid from the servo reservoir to the fluid supply reservoir in response to a predetermined second displacement of the first wall portion relative to the second wall portion. The wall portions of the fluid supply reservoir may be displaceable relative to each other by manual manipulation means or be displaceable relative to each other by manual manipulation means for pushing, pulling, or rotating any of the wall portions of the fluid supply reservoir in one direction. Alternatively, the wall portions of the fluid supply reservoir may be displaceable relative to each other by magnetic means, hydraulic means, manually manipulated means, or electrical control means including an electric motor. The magnetic means, hydraulic means, or electrical control means may all be activated by manually manipulated means preferably located subcutaneously. This control may be indirect, for example via a switch.

Even in the broadest embodiment of the invention the adjustment device may comprise a servo means. The servo means may comprise a hydraulic means, an electric control means, a magnetic means, mechanical means, or a manual manipulating means. The hydraulic means, electric control means, mechanical means or magnetic means may be activated by manual manipulating means. Using a servo system will save the use of force when adjusting the adjustment device which may be of importance in many applications.

All systems according to the invention may be controlled by a wireless remote control.

In accordance with an advantageous embodiment of the invention, there is provided a wireless remote control for controlling the restriction device. The remote control may conveniently comprise an external hand-held remote control unit which is manually operable by the patient to control the restriction device to squeeze and release the colon or rectum or the prolongation thereof. The remote control may advantageously be capable of obtaining information on pressure or other important parameters such as the pressure against the restriction device and of commanding the operation device to operate the adjustment device to adjust the restriction device in response to obtained information. With the remote control the apparatus of the invention is conveniently controlled to adjust the implanted restriction device, which controls the restriction of the fecal passageway and wherein the restriction device is operable to open and close the fecal passageway. With the remote control the restriction device may steplessly controls the cross-sectional area of the passageway.

The apparatus of the invention may further comprise a pressure sensor for directly or indirectly sensing the pressure against the restriction device and the control device may control the restriction device in response to signals from the pressure sensor. The adjustment device preferably non-invasively adjusts the restriction device to change the size of the cross-sectional area.

The adjustment device or other energy consuming components of the apparatus may also be energised with wirelessly transmitted energy from outside the patient's body or with with an implanted battery or accumulator.

The apparatus may further comprise an implanted energy transfer device, wherein the control device releases electric energy and the energy transfer device transfers the electric energy directly or indirectly into kinetic energy for operation of the restriction device.

The remote control comprises means for wireless transfer of energy from outside the patient's body to energy consuming implanted components of the apparatus. A motor may suitably be implanted for operating the operation device and the means for wireless transfer of energy may directly power the motor with transferred energy. The energy transferred by the means for transfer of energy may comprise a wave signal, an electric field or a magnetic field. Preferably, the wireless remote control comprises an external signal transmitter and an implanted signal receiver. For example, the signal transmitter and signal receiver may transmit and receive a signal in the form of digital pulses, which may comprise a magnetic or electric field. Alternatively, which is preferred, the signal transmitter and signal receiver may transmit and receive a wave signal, which may comprise an electromagnetic wave signal, a sound wave signal or a carrier wave signal for a remote control signal. The receiver may comprise a control unit for controlling the hydraulic operation device in response to signals from the signal transmitter.

The apparatus of the invention may further comprise an implanted energizer unit for providing energy to implanted energy consuming components of the apparatus, such as electronic circuits and/or a motor for operating the operation device. The control unit may power such an implanted motor with energy provided by the energizer unit in response to a control signal received from the signal transmitter. Any known or conventional signal transmitting or signal receiving device that is suitable for use with a human or mammal patient may be provided as the signal transmitter or signal receiver. The control signal may comprise an electromagnetic wave signal, such as an infrared light signal, a visible light signal, a laser light signal, a microwave signal, or a sound wave signal, such as an ultrasonic wave signal or an infrasonic wave signal, or any other type of wave signals. The control signal may also comprise electric or magnetic fields, or pulses. All of the above-mentioned signals may comprise digital signals. The control signals may be carried by a carrier signal, which may be the same as the wireless energy signal. Preferably, a digital control signal may be carried by an electromagnetic wave signal. The carrier signal or control signal may be amplitude or frequency modulated.

The motor may be any type of motor, such as a pneumatic, hydraulic or electric motor and the energizer unit may power the motor with pressurized gas or liquid, or electric energy, depending on the type of motor. Where the motor is an electric motor, it may power pneumatic or hydraulic equipment. In all embodiments a motor may be operatively connected to the adjustment device and the control of the motor may be effected by a reversing device implanted in the patient for reversing the function performed by the motor. The reversing device implanted in the patient may also reverse the function performed by the restriction device.

The adjustment device preferably in all embodiments adjusts the restriction device in a non-manual manner without touching the skin of the patient.

The energizer unit may comprise a power supply and the control unit may power the motor with energy from the power supply. Preferably, the power supply is an electric power supply, such as a battery, and the motor is an electric motor. In this case, the battery also continuously powers the circuitry of the signal receiver between the adjustment operations, in order to keep the signal receiver prepared for receiving signals transmitted from the signal transmitter.

The energizer unit may transfer energy from the control signal, as the latter is transmitted to the signal receiver, into electric energy for powering the implanted electronic components. For example, the energizer unit may transfer the energy from the control signal into direct or alternating current.

In case there is an implanted electric motor for operating the operation device the energizer unit may also power the motor with the transferred energy. Advantageously, the control unit directly powers the electric motor with electric energy, as the energizer unit transfers the signal energy into the electric energy. This embodiment is particularly simple and does not require any recurrent invasive measures for exchanging empty power supplies, such as batteries, that is required in the first embodiment described above.

For adjustment devices of the type that requires more, but still relatively low, power for its operation, the energizer unit may comprise a rechargeable electric power supply for storing the electric energy obtained and the control unit may power the electric motor with energy from the rechargeable electric power supply in response to a control signal received from the signal transmitter. In this case, the rechargeable power supply can be charged over a relatively long time (e.g. a few seconds up to a half hour) without powering the electric motor.

The electric power supply suitably comprises an inexpensive simple capacitor. In this case, the electric motor may be a stepping motor.

The signal transmitter may transmit an electromagnetic signal and the energizer unit may draw radiant energy from the electromagnetic wave signal, as the latter is transmitted to the signal receiver, and transfer the radiant energy into electric energy.

Alternatively, the energizer unit may comprise a battery, an electrically operable switch adapted to connect the battery to the signal receiver in an on mode when the switch is powered and to keep the battery disconnected from the signal receiver in a standby mode when the switch is unpowered, and a rechargeable electric power supply for powering the switch. The control unit may power the electric motor with energy from the battery in response to a control signal received from the signal transmitter, when the switch is in its on mode. Advantageously, the energizer unit may transfer wave energy from the control signal, as the latter is transmitted to the signal receiver, into a current for charging the rechargeable electric power supply, which suitably is a capacitor. Energy from the power supply is then used to change the switch from off (standby mode) to on. This embodiment is suited for adjustment devices of the type that require relatively high power for their operation and has the advantage that the electronic circuitry of the signal receiver does not have to be powered by the battery between adjustments. As a result, the life-time of the battery can be significantly prolonged. The switch may be switched with magnetic, manual or electric energy. Preferable the switch is controlled by wireless energy.

As an example, the signal transmitter may transmit an electromagnetic wave signal and the energizer unit may draw radiant energy from the electromagnetic wave signal, as the latter is transmitted to the signal receiver, and may transfer the radiant energy into the current. The energizer unit suitably comprises a coil of the signal receiver for inducing an alternating current as the electromagnetic wave signal is transmitted through the coil and a rectifier for rectifying the alternating current. The rectified current is used for charging the rechargeable power source.

Alternatively, the signal transmitter and receiver may solely be used for a control signal and a further pair of signal transmitter and receiver may be provided for transferring signal energy to implanted components. By such a double system of signal transmitters and receivers the advantage is obtained that the two systems can be designed optimally for their respective purposes, namely to transmit a control signal and to transfer energy from an energy signal. Accordingly, the apparatus may further comprise an external energy transmitter for transmitting wireless energy, wherein the energizer unit comprises a battery and an operable switch for connecting the battery to the signal receiver in an on mode when the switch is powered and for keeping the battery disconnected from the signal receiver in a standby mode when the switch is unpowered, and the external energy transmitter powers the switch. Suitably, the energy transmitter may directly power the switch with the wireless energy to switch into the on mode.

As should be realized by a skilled person, in many of the above-described embodiments of the invention the adjustment device may be operated by control means or manual manipulation means implanted under the skin of the patient, such as a pump, an electrical switch or a mechanical movement transferring means. In the manual embodiment it is not necessary to use a motor for operating the adjustment device.

In accordance with an alternative aspect of the present invention a hydraulic adjustment device adjusts the restriction device to temporarily squeeze the colon or rectum or the prolongation thereof by means of more than one restriction members to restrict the fecal passageway.

In accordance with a further alternative aspect of the present invention it provides an anal incontinence treatment apparatus, comprising an adjustable restriction device implanted in a patient, who suffers from anal incontinence, the restriction device having two restriction members engaging the colon or rectum or the prolongation thereof of the patient to engage the fecal passageway. An adjustment device adjusts the restriction device to temporarily release the colon or rectum or the prolongation thereof and normally to restrict the fecal passageway, and preferable an electrically powered operation device operates the adjustment device in a non-manual manner.

In accordance with another alternative aspect of the present invention there is provided two holding members, one placed more distal than the other, comprising two at least substantially closed loops may be rotated in opposite direction to each other. With interconnecting material for example flexible bands between the holding members a restriction will occure between the holding members when they are rotated.

The restriction device may in all applicable embodiments have any shape or form and be either hydralic or non-inflatable.

Preferably the adjustment device may be engergised directly with wirelessly transmitted energy from outside the patient's body. Preferable, the inplanted energy transfer device transfers wireless energy directly or indirectly into kinetic energy for operation of the restriction device. In another embodiment it would also be possible to use an implanted accumulator or battery and control this implanted energy source from outside the patient's body to supply energy to the adjustment device or other energy consuming parts of the implanted apparatus.

It should be understood that all the applicable embodiments in this application may be combined to achieve alternative embodiments of the invention.

The above described embodiments according to the general aspect of the invention may also be implemented in the described embodiments according to the alternative aspects of the invention, where applicable.

The invention also provides a method for treating a patient suffering from anal incontinence comprising surgically implanting in the body of the an adjustable restriction device which directly engages the colon or rectum to restrict the fecal passageway therein, normally closed, and when desired, mechanically adjusting the restriction device to temporarily open the fecal passageway.

The adjustable restriction device may preferably be inplanted in the base or prolongation of the patients rectum. It is possible to use one or serveral restricting devices engaging the colon or rectum.

In accordance with the invention, there is further provided a method for treating anal incontinence, comprising the steps of placing at least two laparascopical trocars in the body of a patient suffering from anal incontinence, inserting a dissecting tool through the trocars and dissecting an area of the colon or rectum in the abdominal or pelvic or retroperitoneal surroundings, placing at least one adjustable restriction device in the dissected area engaging the rectum or colon, adjusting the restriction device to normally restrict the fecal passageway in the rectum or colon, and adjusting the restriction device to open the fecal passageway when the patient wants to relieve himself or herself. A hydraulic adjustable restriction device may be used when practicing this method, preferably in a non-manual manner, i.e. without touching subcutaneously implanted components of the apparatus.

The method may further comprise implanting a source of energy in the patient and providing a control device for controlling the source of energy from outside the patient's body to supply energy to the restriction device.

The present invention also provides a method for treating anal incontinence, comprising surgically implanting in the body of a patient suffering from anal incontinence an adjustable restriction device engaging the colon or rectum or the prolongation thereof to engage the fecal passageway, and when desired to achieve defaecation, adjusting the restriction device to temporarily release the colon or rectum or the prolongation thereof to open the fecal passageway. The method may further comprise implanting an elongated restriction member of the restriction device around the colon or rectum or the prolongation thereof. In all applications the operation device may be electrically powered.

A further method for treating anal incontinence, comprises surgically implanting in the body of a patient suffering from anal incontinence at least one adjustable restriction devices to affect the fecal passageway engaging respective of the colon or rectum or the prolongation thereof, and when desired to achieve defaecation, non-manually without touching the skin of the patient adjusting the powered restriction device to temporarily release the colon or rectum or the prolongation thereof to open the fecal passageway.

The anal incontinence treatment apparatus may also be laparoscopicily implanted. Thus, in accordance with the invention there is also provided a method comprising placing at least two laparascopical trocars in the body of a patient suffering from anal incontinence, inserting a dissecting tool through the trocars, dissecting an area of the pelvic or abdominal or retroperitoneal surroundings, and placing an adjustable restriction device in the dissected area in engagement with the colon, rectum or the prolongation thereof to restrict the fecal passageway.

The adjustment device may perferable be powered preferable with electricity and operated in a non-manual manner without touching the patients skin.

BRIEF DESCRIPTION OF THE DRAWINGS

FIG. 5A is a perspective view of a hydraulic, pneumatic or mechanical servo system in accordance with a particular embodiment of the principal embodiment shown in FIG. 1D.

FIG. 5B is a cross-sectional view taken along line VB—VB of FIG. 5A.

FIGS. 13A through 17B are five modifications of the embodiment of FIGS. 12A–12C;

DETAILED DESCRIPTION OF THE DRAWINGS

Figure 1A:
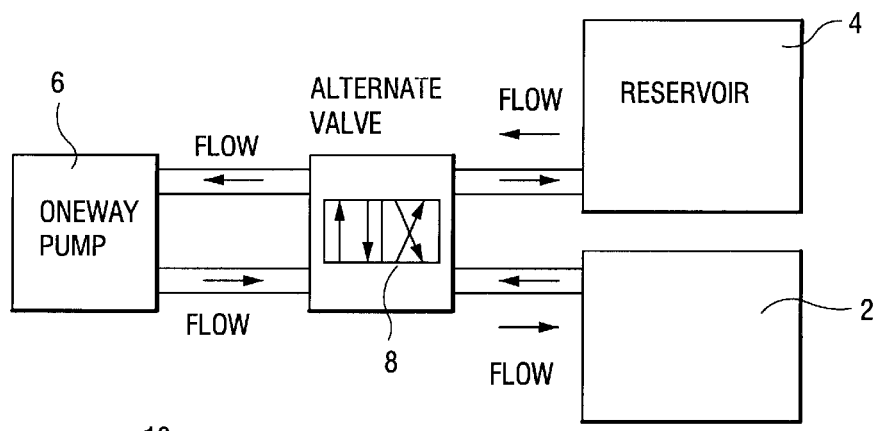
FIGS. 1A–D are block diagrams of four different principal embodiments of the anal incontinence treatment apparatus according to the invention.

Referring to the drawing figures, like reference numerals designate identical or corresponding elements throughout the several figures.

Figure 1B:
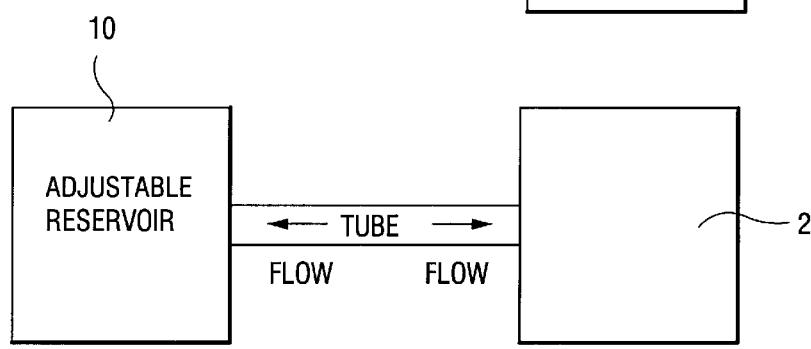
Figure 1C:
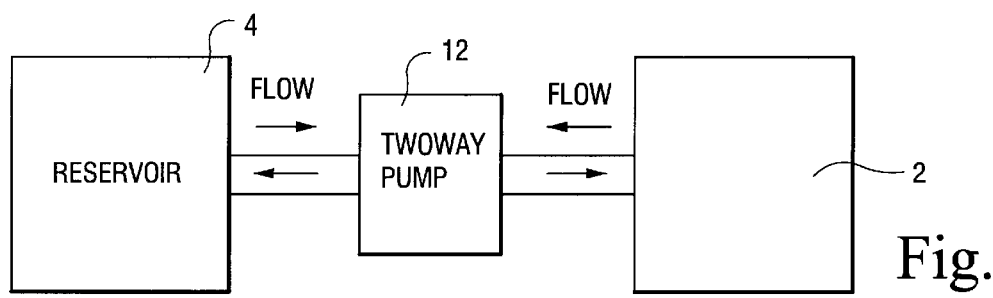
Figure 1D:
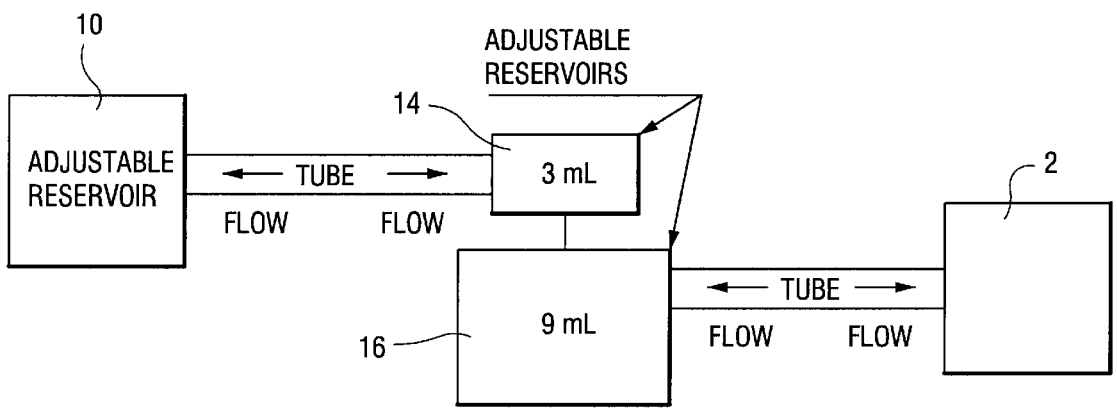
Figure 8:
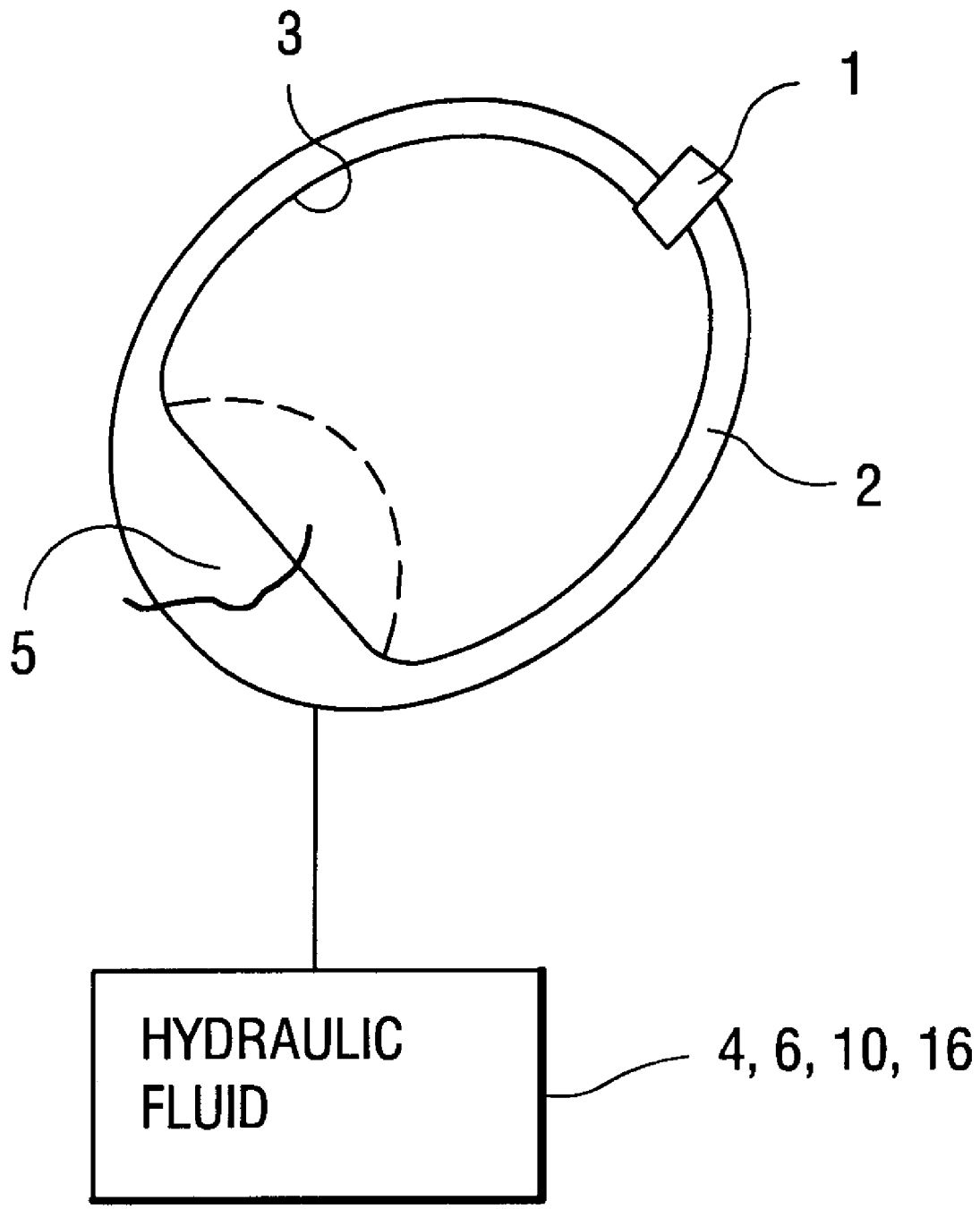
FIG. 8 is a schematic view af a band with a cavity defining a restriction opening for use in accordance with the invention.

FIGS. 1A–D is a block diagram of four different embodiments of the anal incontinence treatment apparatus according to the invention. FIG. 1A shows an elongated restriction member in the form of a band 2 forming a loop which defines a restriction opening. The band 2 provides a restricted fecal passageway in the rectum when applied around the latter. FIG. 1A further shows a separate reservoir 4, a one way pump 6 and an alternate valve 8. FIG. 1B shows the band 2 and a fluid supply reservoir 10. FIG. 1C shows the band 2, a two way pump 12 and the reservoir 4. FIG. 1D shows a servo system with a first closed system controlling a second system. The servo system comprises the fluid supply reservoir 10 and a servo adjustable reservoir 14. The servo reservoir 14 controls a larger adjustable reservoir 16 which in connection with the band 2 applied around the rectum varies the volume of a cavity in the band, which in turn varies the restricted fecal passageway in the rectum. Such a band 2 forming the restriction opening 3 is illustrated schematically in FIG. 8. The band 2 comprises an adjustment device having an expandable/contractabe cavity 5 which is expanded or contracted by supplying hydraulic fluid (e.g. from reservoir 4, 6, 10, or 16), and the band 2 may be sutured in place, illustrated schematically at 7 in FIG 8.

Figure 2A:
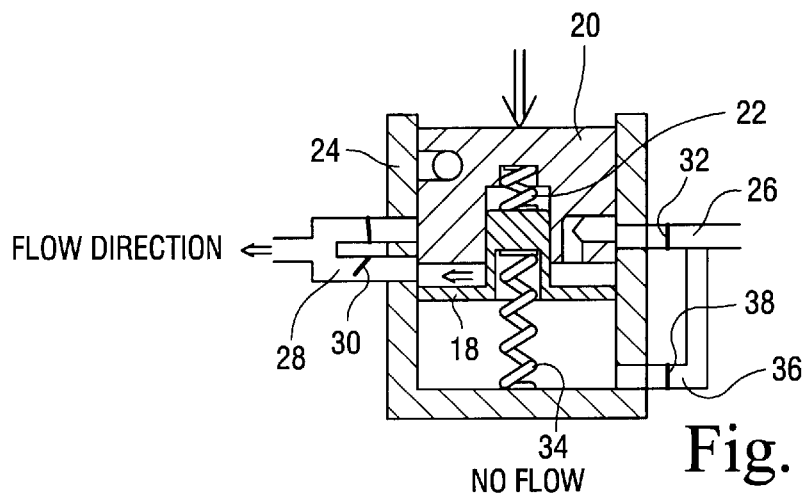
FIGS. 2A–D are cross-sectional views of a pump mechanism according to FIG. 1C, which is designed to pump fluid in opposite directions by mechanically pushing a wall portion in only one direction.
Figure 2B:
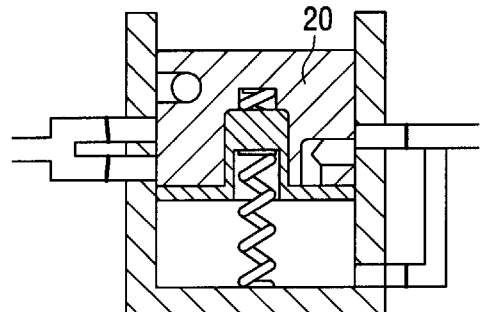
Figure 2C:
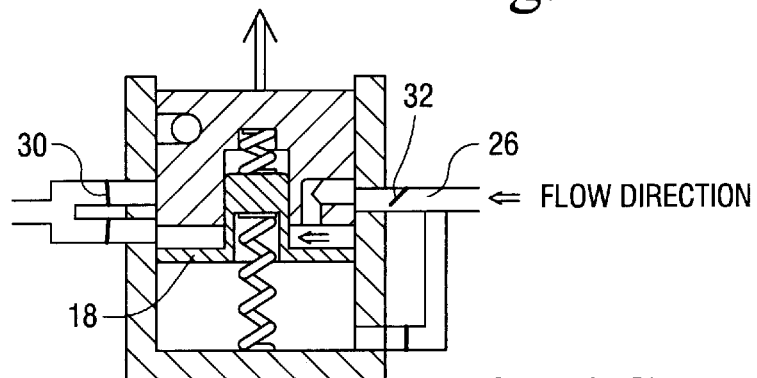
Figure 2D:
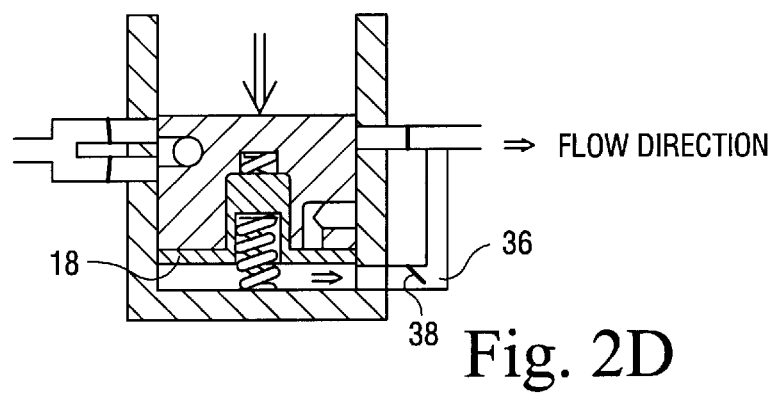

FIGS. 2A–D are cross-sectional views of a pump mechanism adapted to pump fluid in both directions only by mechanically pushing a separate sealing wall portion 18 in one direction. FIG. 2A shows a piston 20 pushed forwards against a spring 22 towards the wall portion 18 and located in a pump housing 24 conducting fluid from a right upper fluid passage 26 of the housing 24 to a left fluid passage 28 of the housing 24. A main valve 30 is open and a nonreturn valve 32 is closed. FIG. 2B illustrates the first pump movement in which the piston 20 has moved forwards and reaches the wall portion 18. FIG. 2C illustrates how the piston 20 moves backwards by the action of the spring 22. The main valve 30 is now closed and the nonreturn valve 32 is open for fluid from the right upper passage 26. FIG. 1D illustrates how the piston 20 is moved further downwards from its position according to FIG. 2B while pushing the wall portion 18 downwardly against a second spring 34 that is stronger than spring 22, whereby fluid escapes from a right lower fluid passage 36. When moving the piston 20 backwardly from the position according to FIG. 2D, fluid enters the left fluid passage 28 and a valve 38 in the lower right fluid passage 36 closes.

Figure 3:
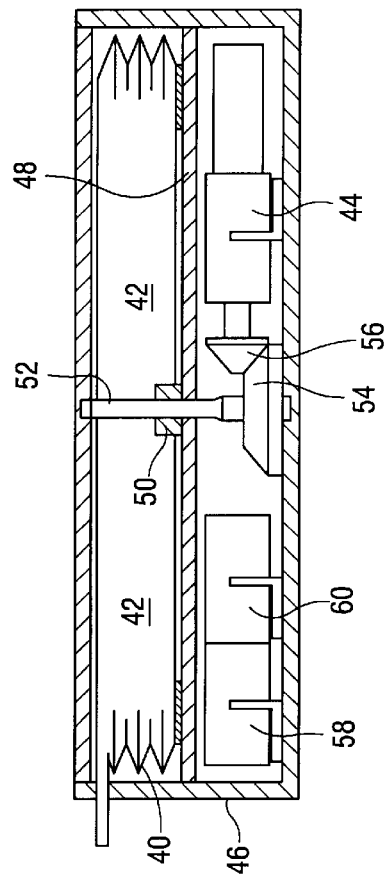
FIG. 3 is a cross-sectional view of a reservoir having a variable volume controlled by a remote control motor, in accordance with a particular embodiment of the principal embodiment shown in FIG. 1B or 2B.

FIG. 3 is a cross-sectional view of a reservoir 40 defining a chamber 42, the size of which is variable and is controlled by a remote controlled electric motor 44, in accordance with FIG. 1B or 1D. The reservoir 40 and the motor 44 are placed in a housing 46. The chamber 42 is varied by moving a large wall 48. The wall 48 is secured to a nut 50, which is threaded on a rotatable spindle 52. The spindle 52 is rotated by the motor 44 via an angular gearing, which comprises two conical gear wheels 54 and 56 in mesh with each other. The motor 44 is powered by a battery 58 placed in the housing 46. An signal receiver 60 for controlling the motor 44 is also placed in the housing 46. Alternatively, the battery 58 and the signal receiver 60 may be mounted in a separate place. The motor 44 may also be powered by energy transferred from transmitted signals.

Figure 4:
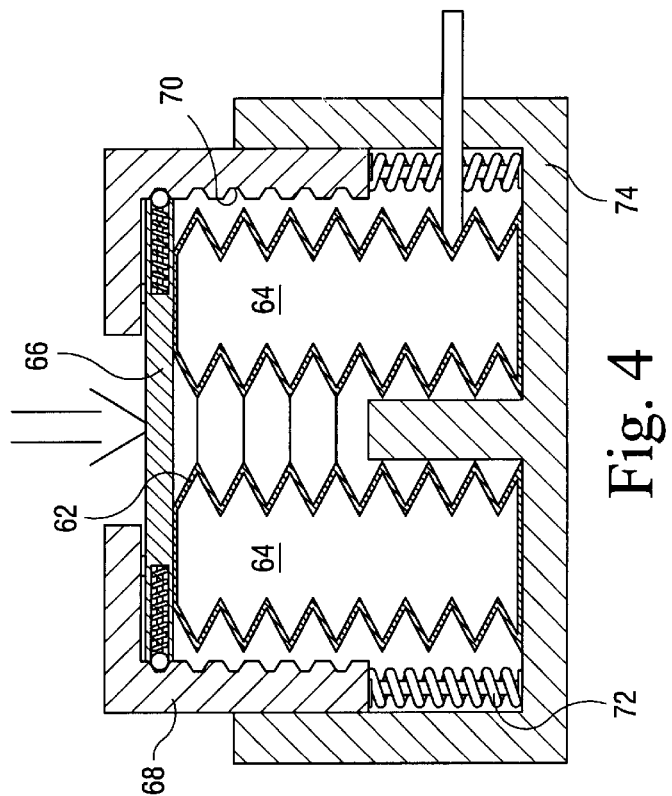
FIG. 4 is a cross-sectional view of a reservoir having a variable volume adjustable by manual manipulation, in accordance with a particular embodiment of the principal embodiment shown in FIG. 1B or 1D.

FIG. 4 is a cross-sectional view of a reservoir 62 defining a chamber 64, the size of which is variable and is controlled by manual manipulation. A gable wall portion 66 of an open ended inner cylindrical housing 68 is adapted to be pushed downwards to fit in a desired locking groove 70 of a plurality of locking grooves 70 on the mantle wall of the cylindrical housing 68, to reduce the size of the chamber 64. The inner cylindrical housing 68 is suspended by springs 72 and is telescopically applied on an outer cylindrical housing 74. When pushing the inner cylindrical housing 68 it moves downwards relative to the outer cylindrical housing 74 causing the gable wall portion 66 to release from the locking groove 70 and move upwards relative to the inner cylindrical housing 68. When the inner housing 68 is moved upwardly by the action of the springs 72 the size of the chamber 64 is increased.

FIGS. 5A and 5B show a servo means comprising a main ring-shaped fluid reservoir 76 defining a chamber 78, the size of which is variable. Centrally positioned in the main ring-shaped reservoir 76 there is a servo fluid reservoir 80 defining a chamber 82, the size of which is variable. The chamber 82 of the servo reservoir 80 is substantially smaller than the chamber 78 of the main reservoir 76. The two reservoirs 76 and 80 are situated between two opposite separate walls 84 and 86, and are secured thereto. When changing the amount of fluid in the servo reservoir 80, the two opposite walls 84,86 are moved towards or away from each other, whereby the size of the chamber 78 of the main reservoir 76 is changed.

Figure 6:
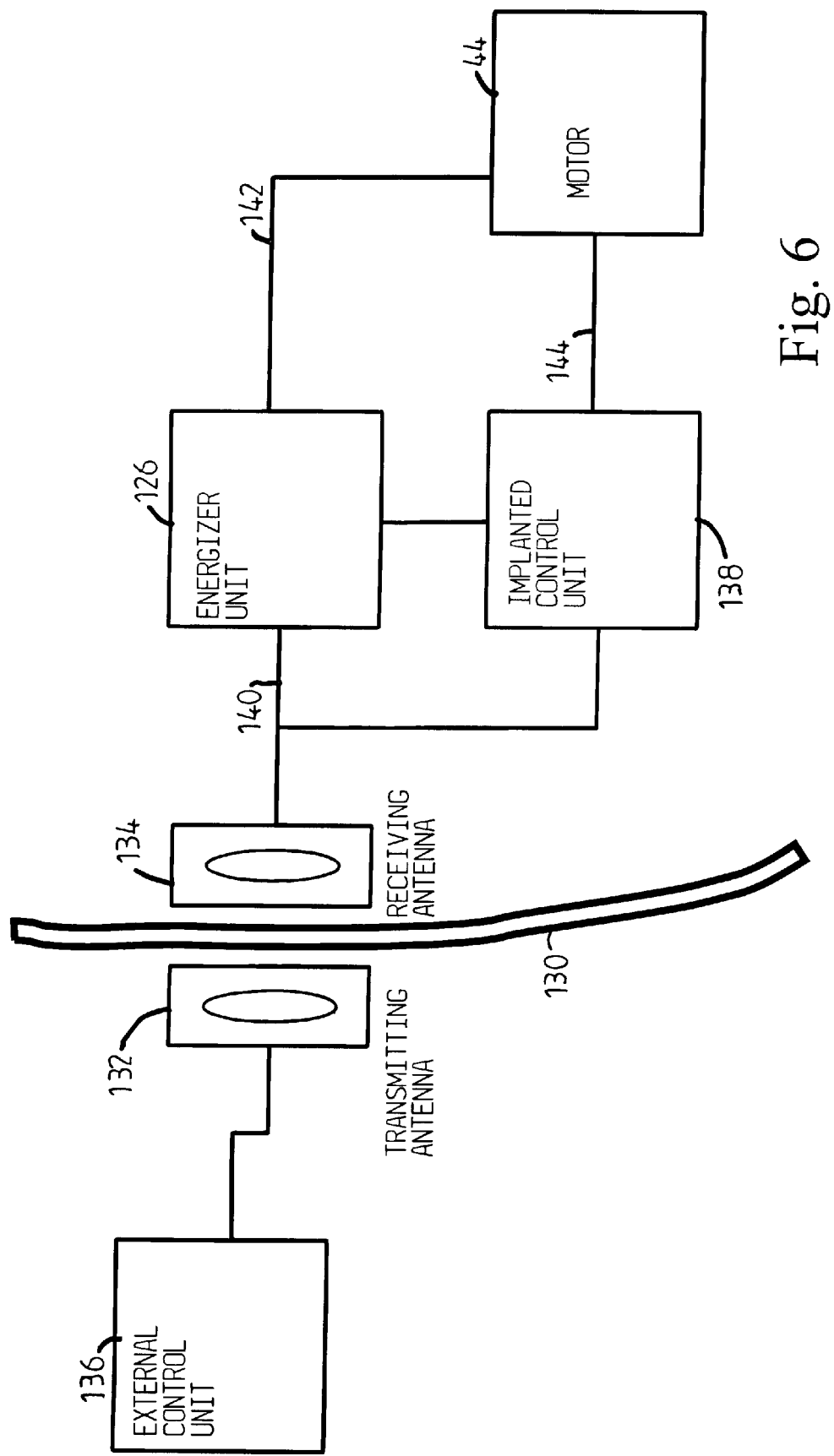
FIG. 6 is a block diagram illustrating remote control components of the device of the invention.

FIG. 6 shows the basic parts of a remote control system of the apparatus of the invention including the electric motor 44 of the embodiment shown in FIG. 3. In this case, the remote control system is based on the transmission of electromagnetic wave signals, often of high frequencies in the order of 100 kHz–1 gHz, through the skin 130 of the patient. In FIG. 6, all parts placed to the left of the skin 130 are located outside the patient's body and all parts placed to the right of the skin 130 are implanted. Any suitable remote control system may be used.

An external signal transmitting antenna 132 is to be positioned close to a signal receiving antenna 134 implanted close to the skin 130. As an alternative, the receiving antenna 134 may be placed for example inside the abdomen of the patient. The receiving antenna 134 comprises a coil, approximately 1–100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The transmitting antenna 132 comprises a coil having about the same size as the coil of the receiving antenna 134 but wound with a thick wire that can handle the larger currents that is necessary. The coil of the transmitting antenna 132 is tuned to the same specific high frequency as the coil of the receiving antenna 134.

An external control unit 136 comprises a microprocessor, a high frequency electromagnetic wave signal generator and a power amplifier. The microprocessor of the control unit 136 is adapted to switch the generator on/off and to modulate signals generated by the generator to send digital information via the power amplifier and the antennas 132,134 to an implanted control unit 138. To avoid that accidental random high frequency fields trigger control commands, digital signal codes are used. A conventional keypad placed on the external control unit 136 is connected to the microprocessor thereof. The keypad is used to order the microprocessor to send digital signals to either increase or decrease the size of the restriction opening defined by the loop of the restriction member 2. The microprocessor starts a command by applying a high frequency signal on the antenna 132. After a short time, when the signal has energized the implanted parts of the control system, commands are sent to increase or decrease the size of the restriction opening of the restriction member 2 in predefined steps. The commands are sent as digital packets in the form illustrated below.

| Start pattern, 8 bits | Command, 8 bits | Count, 8 bits | Checksum, 8 bits |
| --- | --- | --- | --- |

The commands are sent continuously during a rather long time period (e.g. about 30 seconds or more). When a new increase or decrease step is desired the Count byte is increased by one to allow the implanted control unit 138 to decode and understand that another step is demanded by the external control unit 136. If any part of the digital packet is erroneous, its content is simply ignored.

Through a line 140, an implanted energizer unit 126 draws energy from the high frequency electromagnetic wave signal received by the receiving antenna 134. The energizer unit 126 stores the energy in a power supply, such as a large capacitor, powers the control unit 138 and powers the electric motor 44 via a line 142.

The control unit 138 comprises a demodulator and a microprocessor. The demodulator demodulates digital signals sent from the external control unit 136. The microprocessor of the control unit 138 receives the digital packet, decodes it and, provided that the power supply of the energizer unit 126 has sufficient energy stored, sends a signal via a signal line 144 to the motor 44 to either increase or decrease the size of the restriction opening of the restriction member 2 depending on the received command code.

Alternatively, the energy stored in the power supply of the energizer unit may only be used for powering a switch, and the energy for powering the motor 44 may be obtained from another implanted power source of relatively high capacity, for example a battery. In this case the switch is adapted to connect the battery to the control unit 138 in an on mode when the switch is powered by the power supply and to keep the battery disconnected from the control unit in a standby mode when the switch is unpowered.

Figure 7:
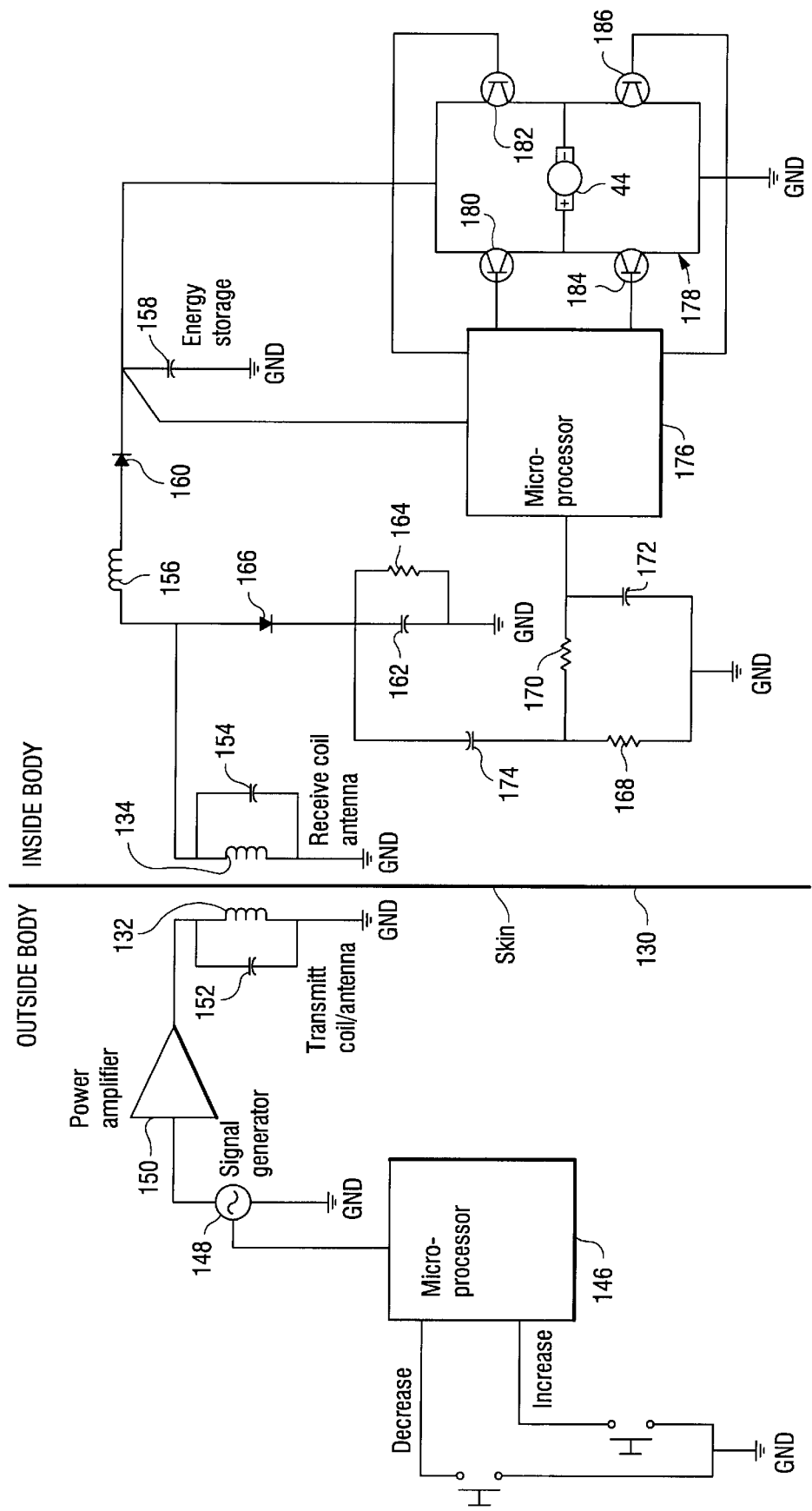
FIG. 7 is a schematic view of exemplary circuitry used for the block diagram in FIG. 4.

With reference to FIG. 7, the remote control system schematically described above will now be described in accordance with a more detailed embodiment. The external control unit 136 comprises a microprocessor 146, a signal generator 148 and a power amplifier 150 connected thereto. The microprocessor 146 is adapted to switch the signal generator 148 on/off and to modulate signals generated by the signal generator 148 with digital commands that are sent to implanted components of the anal incontinence apparatus. The power amplifier 150 amplifies the signals and sends them to the external signal transmitting antenna 132. The antenna 132 is connected in parallel with a capacitor 152 to form a resonant circuit tuned to the frequency generated by the signal generator 148.

The implanted signal receiving antenna coil 134 forms together with a capacitor 154 a resonant circuit that is tuned to the same frequency as the transmitting antenna 132. The signal receiving antenna coil 134 induces a current from the received high frequency electromagnetic waves and a rectifying diode 160 rectifies the induced current, which charges a storage capacitor 158. A coil 156 connected between the antenna coil 134 and the diode 160 prevents the capacitor 158 and the diode 160 from loading the circuit of the signal receiving antenna 134 at higher frequencies. Thus, the coil 156 makes it possible to charge the capacitor 158 and to transmit digital information using amplitude modulation.

A capacitor 162 and a resistor 164 connected in parallel and a diode 166 forms a detector used to detect amplitude modulated digital information. A filter circuit is formed by a resistor 168 connected in series with a resistor 170 connected in series with a capacitor 172 connected in series with the resistor 168 via ground, and a capacitor 174, one terminal of which is connected between the resistors 168, 170 and the other terminal of which is connected between the diode 166 and the circuit formed by the capacitor 162 and resistor 164. The filter circuit is used to filter out undesired low and high frequencies. The detected and filtered signals are fed to an implanted microprocessor 176 that decodes the digital information and controls the motor 44 via an H-bridge 178 comprising transistors 180, 182, 184 and 186. The motor 44 can be driven in two opposite directions by the H-bridge 178.

The microprocessor 176 also monitors the amount of stored energy in the storage capacitor 158. Before sending signals to activate the motor 44, the microprocessor 176 checks whether the energy stored in the storage capacitor 158 is enough. If the stored energy is not enough to perform the requested operation, the microprocessor 176 waits for the received signals to charge the storage capacitor 158 before activating the motor 44.

Figure 9A:
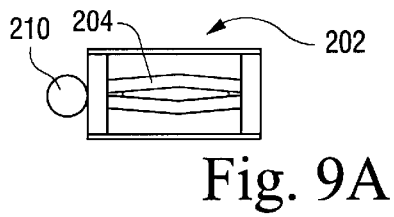
FIGS. 9A and 9B are schematic views of a first mechanical restriction device for use in accordance with the invention.
Figure 9B:
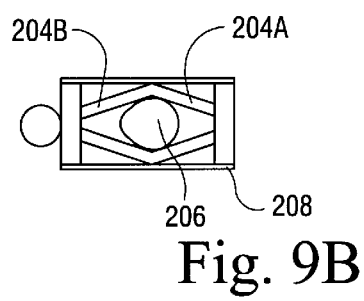

FIGS. 9A and 9B show an embodiment of the apparatus of the invention comprising a restriction device 202 having an elongated flexible restriction member 204, such as a belt, a cord or the like. The flexible member 204 extends in a loop around the rectum. (Alternatively, the flexible member 204 may comprise two separate parts on opposite sides of the rectum.) One portion 204A of member 204 is attached to a frame 208 and another portion 204B of member 204 opposite portion 204A in the loop of the flexible member 204 is connected to an adjustment device 210, which is fixed to the frame 208. The adjustment device 210 pulls the flexible member 204 away from portion 204A to squeeze the rectum between two opposite lengths of the flexible member 204 to thereby restrict the fecal passageway, see FIG. 96A, and releases the rectum from the flexible member 204 to thereby increase the fecal passageway, see FIG. 9B.

Figure 10A:
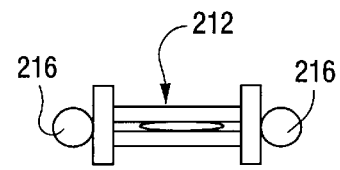
FIGS. 10A and 10B are schematic views of a second mechanical restriction device for use in accordance with the invention.
Figure 10B:
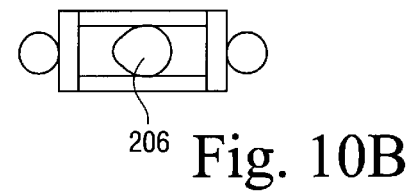

FIGS. 10A and 10B show an embodiment of the apparatus of the invention comprising a restriction device 212 having two plate or bar elements 214 on opposite sides of the rectum 206. An adjustment device 216 moves the elements 212 in parallel towards each other to squeeze the rectum 206 between the elements 212 to thereby restrict the fecal passageway, see FIG. 10A, and moves the elements 212 away from each other to increase the fecal passageway, see FIG. 10B.

Figure 11:
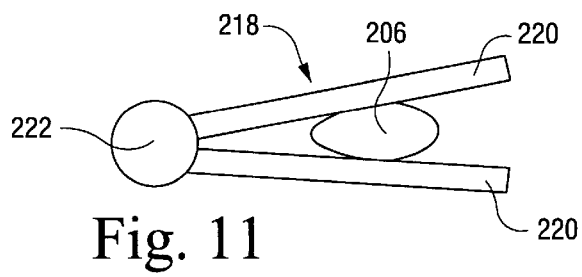
FIG. 11 is a schematic view of a third mechanical restriction device for use in accordance with the invention.

FIG. 11 shows an embodiment of the apparatus of the invention comprising a restriction device 218 having two articulated clamping elements 220 positioned on opposite sides of the rectum 206. An adjustment device 222 moves the clamping elements 220 toward each other to clamp the rectum 206 between the clamping elements 220 to thereby restrict the fecal passageway, and moves the clamping elements 220 away from each other to release the rectum 206 from the clamping elements 220 to thereby increase the fecal passageway.

Figure 12A:
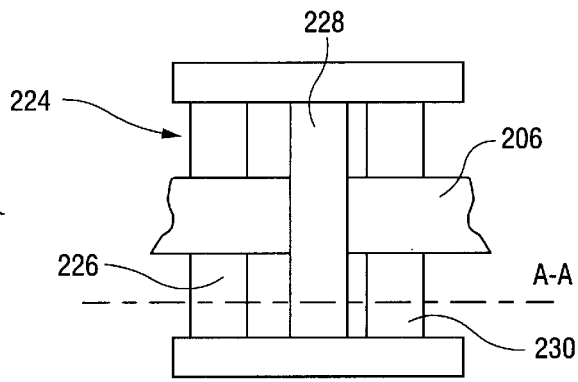
FIG. 12A is a schematic front view of a fourth mechanical restriction device for use in accordance with the invention.
Figure 12B:
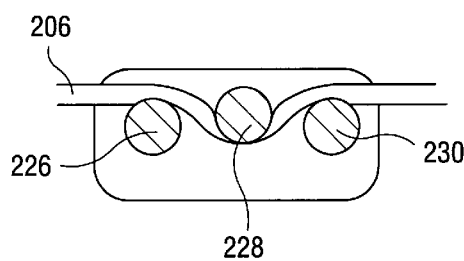
FIGS. 12B and 12C are sectional views along the line A—A of FIG. 12A.
Figure 12C:
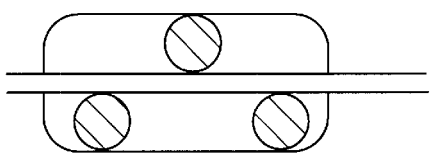
Figure 16A:
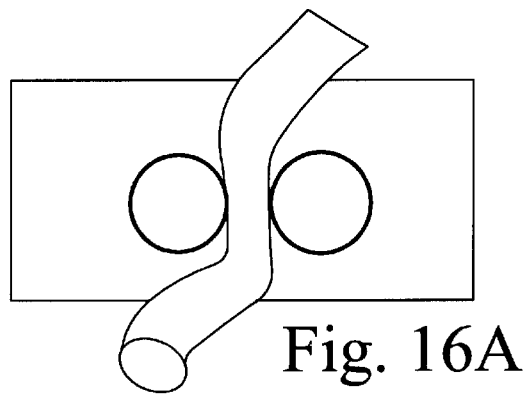
Figure 16B:
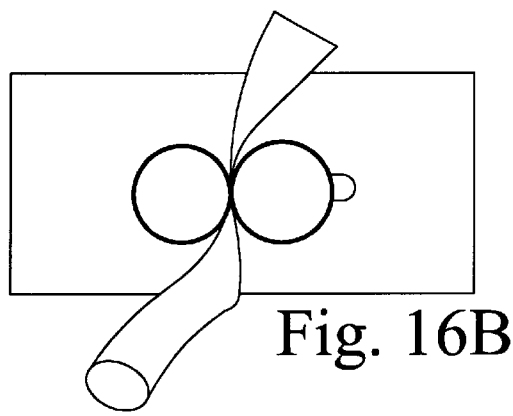

FIGS. 12A, 12B and 12C show an embodiment of the apparatus of the invention comprising a restriction device 224 having three bending members in the form of cylindrical rollers 226, 228 and 230 displaced relative one another in a row along the rectum 206 and positioned alternately on opposite sides of the rectum 206. (Alternatively, each roller 226, 228 and 230 may take the shape of an hour-glass.) An adjustment device 232 moves the two outer rollers 226, 230 laterally against the rectum 206 in one direction and the intermediate roller 228 against the rectum 206 in the opposite direction to bend the rectum to thereby restrict the fecal passageway, see FIG. 12B. To release the rectum from the rollers 226–230, the adjustment device 232 moves the rollers 226–230 away from the rectum 206, see FIG. 12C.

Figure 17A:
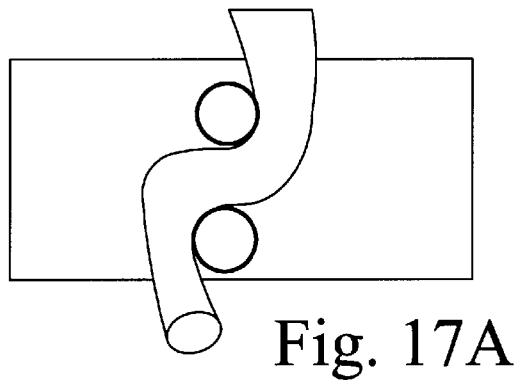
Figure 17B:
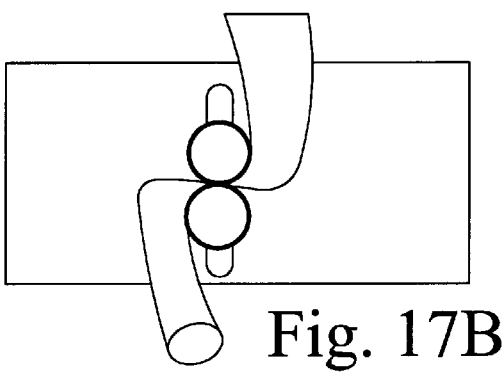

FIGS. 13A through 17B schematically illustrates modifications of the above embodiment according to FIGS. 12A–12C. Thus, FIGS. 13A and 13B show an embodiment similar to that of FIGS. 12A–12C except that the bending members are oval and not rotatable. FIGS. 14A and 14B show an embodiment similar to that of FIGS. 13A and 13B except that the oval bending members are rotatable to squeeze the rectum, see FIG. 14B, and to release the rectum, see FIG. 14A. FIGS. 15A and 15B show an embodiment similar to that of FIGS. 12A–12C except that the intermediate roller has a changeable diameter to squeeze the rectum, see FIG. 15B, and to release the rectum, see FIG. 15A. FIGS. 16A and 16B show an embodiment similar to that of FIGS. 10A–10C except that the elements are replaced by two cylindrical rollers positioned on opposite sides of the rectum. Finally, FIGS. 17A and 17B show an embodiment substantially similar to that of FIGS. 16A and 16B except that the restriction device is turned 90_to form a S-shaped curvature of the rectum.

Figure 18:
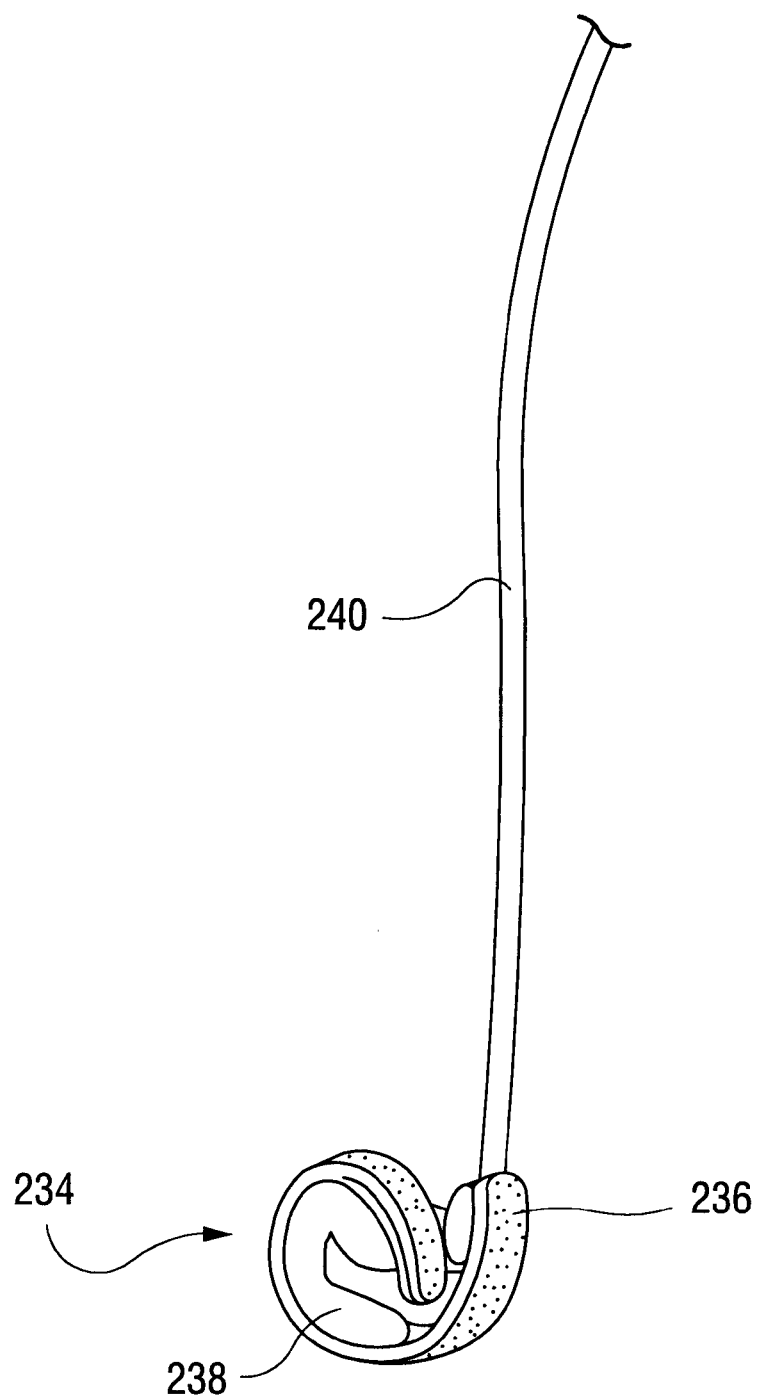
FIG. 18 is a view of an inflatable restriction device of the apparatus of the invention.

FIG. 18 shows an example of a hudraulic restriction device 234 for use in accordance with the invention. The restriction device 234 comprises an elongated restriction member 236 having an inflatable cavity 238. A tube 240 connects the cavity 238 to a hydraulic fluid reservoir, not shown. The restriction member 236 may be wrapped around the rectum.

Figure 19:
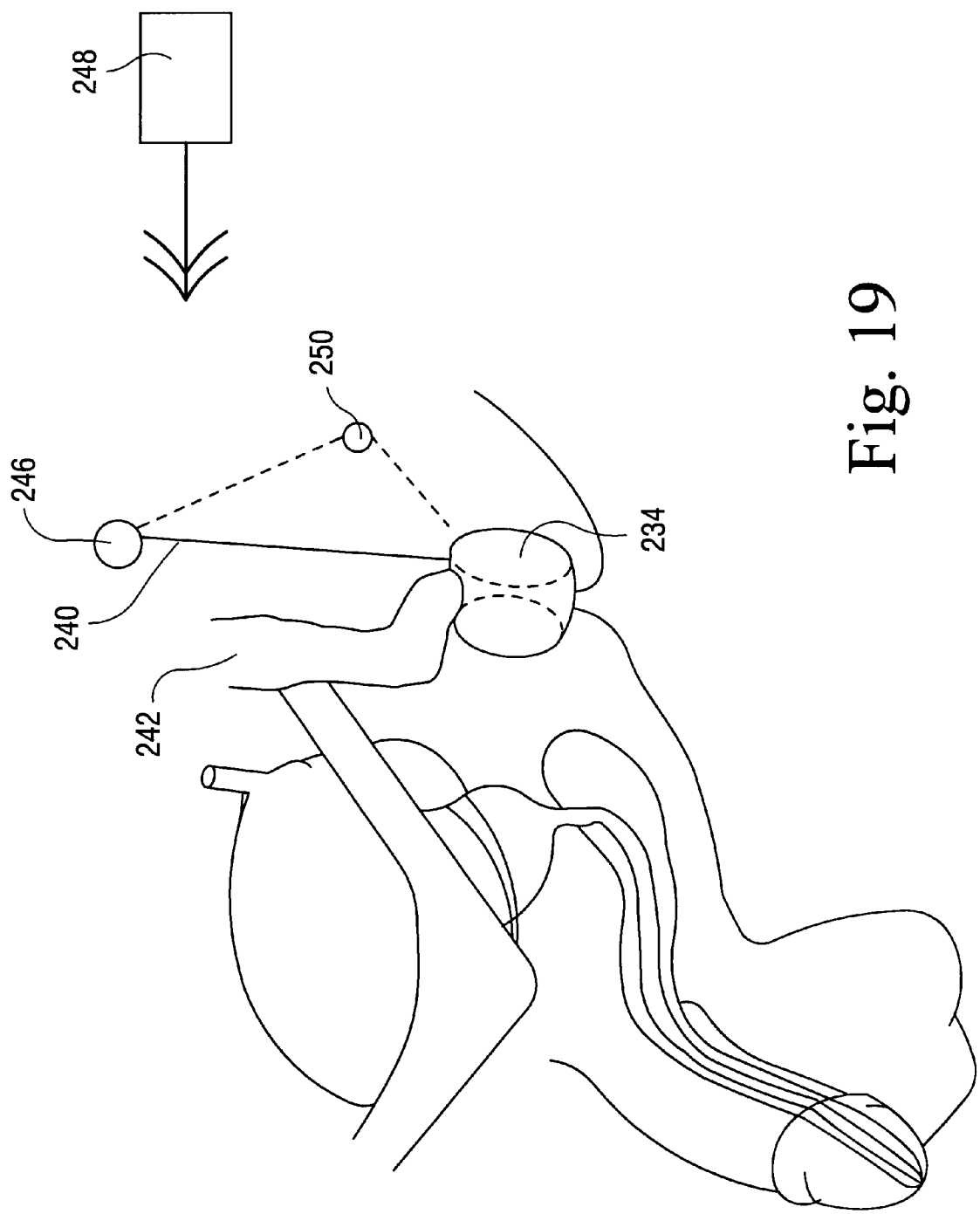
FIG. 19 illustrates the apparatus of the invention implanted in a patient.

FIG. 19 schematically illustrates how any of the above-described embodiments of the anal incontinence treatment apparatus of the invention can be implanted in a patient. Thus, an implanted adjustable hydraulic restriction device 234 extends almost completely around the rectum 242 to be capable of squeezing the rectum 242 as a single unit. An adjustment device in the form of an inflatable cavity in the restriction device 234 is adapted to adjust the restriction device 234 so that the fecal passageway is restricted. An implanted assembly 246 includes a hydraulic fluid reservoir and an operation device (which may include a pump) for distributing hydraulic fluid between the reservoir and the inflatable/contractible cavity of the restriction device 234 via a fluid conduit 240. A wireless remote control of the apparatus comprises an external signal transmitter 248, which may comprise a hand-held unit, and an implanted signal receiver, which is incorporated in the implanted assembly 246, includes a control unit for controlling the restriction device 234 in response to a control signal from the external transmitter. The signal receiver of the assembly 246 further includes an energizer unit which transfers energy from the control signal transmitted by the external transmitter into electric energy for energy consuming implanted components of the apparatus.

A pressure sensor 250 is implanted for sensing the pressure on the restriction device 234. The control unit of the signal receiver of the implanted assembly 246 controls the restriction device 436 to release the restriction device 434 in response to the pressure sensor 439 sensing an abnormal high pressure.

There are a number of conceivable alternative embodiments of the invention that give the same result as the above-described embodiments. For example, the microprocessor of the external and implanted, respectively, control units may be replaced by discrete components. The power amplifier of the external control unit may be omitted if the signals generated by the signal generator are strong enough. Therefore, the invention is to be accorded the broadest interpretation of the appended claims to encompass all equivalent structures and assemblies.

What is claimed is:

1. An anal incontinence treatment apparatus, comprising:
    an adjustable restriction device adapted to be implanted in a patient, who suffers from anal incontinence, to constrict the colon or rectum or the prolongation thereof to restrict the fecal passageway therein,
    an adjustment device adapted to be implanted in the patient for adjusting said restriction device to restrict the fecal passageway to prevent feces from passing therethrough and enlarge the fecal passageway to allow feces to readily pass therethrough,
    an electrically powered hydraulic operation device adapted to be implanted in the patient for operating said adjustment device, and
    energy transfer means for transferring, directly or indirectly, wireless energy into electric energy for powering said hydraulic operation device.

2. The apparatus according to claim 1, wherein said restriction device is adapted to control the restriction of the fecal passageway.

3. The apparatus according to claim 2, wherein said restriction device is adapted to control the restriction of the fecal passageway to change steplessly.

4. The apparatus according to claim 2, wherein said adjustment device is adapted to adjust said restriction device such that the fecal passageway is restricted in a predetermined extent that is satisfactory for the patient.

5. The apparatus according to claim 1, further comprising a control device for controlling said restriction device.

6. The apparatus according to claim 5, wherein said control device comprises an internal control unit adapted to be implanted in the patient for controlling said restriction device.

7. The apparatus according to claim 6, wherein said internal control unit is programmable.

8. The apparatus according to claim 7, wherein said control device comprises an external control unit outside the patient's body and said internal control unit is programmable by said external control unit.

9. The apparatus according to claim 5, wherein said control device comprises an external control unit outside the patient's body adapted to wirelessly control said restriction device.

10. The apparatus according to claim 9, wherein said external control unit is programmable.

11. The apparatus according to claim 1, further comprising at least one sensor adapted to be implanted in the patient for sensing at least one physical parameter of the patient.

12. The apparatus according to claim 11, wherein said sensor is adapted to sense the pressure against the restriction device, directly or indirectly, and said restriction device is adapted to release the restriction of the fecal passageway in response to said sensor sensing a predetermined pressure value.

13. The apparatus according to claim 11, further comprising a control device controlling said restriction device in response to signals from said sensor.

14. The apparatus according to claim 13, wherein said control device comprises an internal control unit adapted to be implanted in the patient and directly controlling said restriction device in response to signals from said sensor.

15. The apparatus according to claim 13, wherein said control device comprises an external control unit outside the patient's body controlling said restriction device in response to signals from said sensor.

16. The apparatus according to claim 1, wherein said adjustment device adjusts said restriction device in a non-magnetic manner.

17. The apparatus according to claim 1, wherein said restriction device comprises an elongated restriction member and forming means for forming said restriction member into at least a substantially closed loop around the colon or rectum or the prolongation thereof, said loop defining a restriction opening, whereby said adjustment device adjusts said restriction member in said loop to change the size of said restriction opening.

18. The apparatus according to claim 17, wherein said forming means forms said restriction member into a loop having a predetermined size.

19. The apparatus according to claim 17, wherein said elongated restriction member is flexible, and said adjustment device is adapted to pull a first portion of said flexible restriction member from a second portion of said flexible restriction member opposite said first portion in said loop to squeeze the colon or rectum between two opposite lengths of said elongated flexible restriction member to restrict the fecal passageway.

20. The apparatus according to claim 19, wherein said elongated restriction member is non-inflatable, and said adjustment device mechanically adjusts said restriction member in said loop.

21. The apparatus according to claim 17, wherein said adjustment device changes the size of said restriction opening such that the outer circumferential confinement surface of said restriction member is changed.

22. The apparatus according to claim 17, wherein said adjustment device changes the size of said restriction opening such that the outer circumferential confinement surface of said restriction member is unchanged.

23. The apparatus according to claim 1, wherein said restriction device comprises at least two elements adapted to be positioned on different sides of the colon or rectum or the prolongation thereof, and said adjustment device is adapted to squeeze the colon or rectum or the prolongation thereof between said elements to restrict the fecal passageway.

24. The apparatus according to claim 1, wherein said restriction device comprises at least two articulated clamping elements adapted to be positioned on opposite sides of the colon or rectum or the prolongation thereof, and said adjustment device is adapted to move said clamping elements toward each other to clamp the colon or rectum or the prolongation thereof between said clamping elements to restrict the fecal passageway.

25. The apparatus according to claim 1, wherein said restriction device is adapted to bend the colon or rectum or the prolongation thereof.

26. The apparatus according to claim 25, wherein said restriction device comprises at least two bending members adapted to be positioned on opposite sides of the colon or rectum or the prolongation thereof, and said adjustment device is adapted to move said bending members against the colon or rectum or the prolongation thereof in two opposite spaced apart directions to bend the colon or rectum or the prolongation thereof to restrict the fecal passageway.

27. The apparatus according to claim 26, wherein said bending members comprise rollers.

28. The apparatus according to claim 1, further comprising a reservoir adapted to be implanted in the patient and containing a predetermined amount of hydraulic fluid, wherein said hydraulic operation device operates said adjustment device by using said hydraulic fluid of said reservoir.

29. The apparatus according to claim 28, wherein said adjustment device comprises an expandable cavity in said restriction device, the colon or rectum or the prolongation thereof being constricted upon expansion of said cavity and released upon contraction of said cavity, and said hydraulic operation device distributes hydraulic fluid from said reservoir to expand said cavity and distributes hydraulic fluid from said cavity to said reservoir to contract said cavity.

30. The apparatus according to claim 29, wherein said reservoir defines a chamber for said predetermined amount of fluid and said hydraulic operation device changes the size of said chamber.

31. The apparatus according to claim 30, wherein said hydraulic operation device comprises first and second wall portions of said reservoir, which are displaceable relative to each other to change the size of said chamber of said reservoir.

32. The apparatus according to claim 31, wherein said first and second wall portions of said reservoir are displaceable relative to each other by non-manual manipulation thereof.

33. The apparatus according to claim 31, wherein said first and second wall portions of said reservoir are displaceable relative to each other by magnetic means, hydraulic means, or electric control means.

34. The apparatus according to claim 31, wherein said hydraulic operation device distributes fluid from said reservoir to said cavity in response to a predetermined first displacement of said first wall portion of said reservoir relative to said second wall portion of said reservoir and distributes fluid from said cavity to said reservoir in response to a predetermined second displacement of said first wall portion relative to said second wall portion.

35. The apparatus according to claim 29, wherein said hydraulic operation device comprises a pump for pumping fluid between said reservoir and said cavity.

36. The apparatus according to claim 35, wherein said pump comprises. a first activation member for activating said pump to pump fluid from said reservoir to said cavity and a second activation member for activating said pump to pump fluid from said cavity to said reservoir.

37. The apparatus according to claim 36, wherein said first and second activation members are operable by manual manipulation thereof.

38. The apparatus according to claim 36, wherein at least one of said activation members operates when subjected to an external predetermined pressure.

39. The apparatus according to claim 36, wherein at least one of said first and second activation members are operable by magnetic means, hydraulic means, or electric control means.

40. The apparatus according to claim 35, wherein said operation device comprises a fluid conduit between said pump and said cavity, said reservoir forming part of said conduit.

41. The apparatus according to claim 40, wherein said conduit and pump are devoid of any non-return valve.

42. The apparatus according to claim 41, wherein said reservoir forms a fluid chamber with a variable volume, and said pump distributes fluid from said chamber to said cavity by reduction of the volume of said chamber and withdraws fluid from said cavity by expansion of the volume of said chamber.

43. The apparatus according to claim 42, wherein said operation device comprises a motor for driving said pump.

44. The apparatus according to claim 43, wherein said pump comprises a movable wall of said reservoir for changing the volume of said chamber.

45. The apparatus according to claim 1, further comprising a wireless remote control for controlling said restriction device.

46. The apparatus according to claim 45, wherein said remote control comprises an external wireless hand-held remote control unit which is manually operable by the patient to control said restriction device to vary the restriction of the fecal passageway.

47. The apparatus according to claim 45, wherein said remote control comprises an external signal transmitter or receiver and a signal receiver or transmitter adapted to be implanted in the patient.

48. The apparatus according to claim 47, wherein said signal transmitter and signal receiver transmit and receive a wave signal.

49. The apparatus according to claim 48, wherein said wave signal comprises an electromagnetic wave signal, a sound wave signal or a carrier wave signal for a remote control signal.

50. The apparatus according to claim 47, wherein said signal receiver comprises a control unit for controlling said restriction device in response to a control signal received from said signal transmitter.

51. The apparatus according to claim 50, further comprising an energizer unit adapted to be implanted in the patient for providing electric energy to energy consuming implantable components of the apparatus.

52. The apparatus according to claim 51, further comprising an electric motor adapted to be implanted in the patient for driving said hydraulic operation device.

53. The apparatus according to claim 52, wherein said control unit controls said energizer unit to power said electric motor with electric energy in response to a control signal received from said signal transmitter.

54. The apparatus according to claim 51, wherein said energizer unit transfers energy from said control signal, as the latter is transmitted to said signal receiver, into electric energy.

55. The apparatus according to claim 54, wherein said energizer unit transfers the energy from said signal into a direct or alternating current.

56. The apparatus according to claim 54, further comprising a reversing device adapted to be implanted in the patient for reversing said electric motor.

57. The apparatus according to claim 47, wherein said signal transmitter and signal receiver transmit and receive a signal in the form of digital pulses.

58. The apparatus according to claim 57, wherein said digital pulses comprise a magnetic field or an electric field.

59. The apparatus according to claim 1, wherein said energy transfer means transfers wireless energy into electric energy that is supplied to energy consuming implantable components of the apparatus.

60. The apparatus according to claim 59, further comprising an electric motor adapted to be implanted in the patient for driving said hydraulic operation device, wherein said energy transfer means directly, during energy transfer, powers said electric motor with transferred electric energy.

61. The apparatus according to claim 60, wherein said energy transfer means transfers wireless energy in the form of a wave signal.

62. The apparatus according to claim 60, wherein said energy transfer means transfers wireless energy in the form of an electric field or a magnetic field.

63. The apparatus according to claim 45, wherein said remote control is capable of obtaining information related to important parameters from inside the patients body and of commanding said adjustment device to adjust said restriction device in response to obtained information.

64. The apparatus according to claim 45, wherein said remote control is capable of obtaining information from implanted components of the apparatus and of commanding said adjustment device to adjust said restriction device in response to obtained information.

65. The apparatus according to claim 1, further comprising a pressure sensor adapted to be implanted in the patient for directly or indirectly sensing the pressure against the restriction device.

66. The apparatus according to claim 1, further comprising a battery or accumulator adapted to be implanted in the patient for energizing energy consuming implantable components of the apparatus, wherein said battery or accumulator is adapted to be controlled from outside the patient's body to release energy.

67. The apparatus according to claim 1, wherein energy consuming implantable components of the apparatus are adapted to be energized with energy wirelessly transmitted from outside the patient's body.

68. The apparatus according to claim 67, further comprising an electric motor adapted to be implanted in the patient for driving said hydraulic operation device, wherein said energy wirelessly transmitted from outside the patient's body comprises electric energy for powering said electric motor.

69. The apparatus according to claim 68, wherein said electric energy wirelessly transmitted comprises electromagnetic or sound waves.

70. The apparatus according to claim 1, further comprising an electric motor adapted to be implanted in the patient for driving said hydraulic operation device.

71. An anal incontinence treatment apparatus, comprising:

an adjustable non-inflatable restriction device adapted to be implanted in a patient, who suffers from anal incontinence, to constrict the colon or rectum or the prolongation thereof to restrict the fecal passageway therein, a hydraulic adjustment device adapted to be implanted in the patient for adjusting said restriction device to restrict the fecal passageway to prevent feces from passing therethrough and to enlarge the fecal passageway to allow feces to readily pass therethrough, an implantable reservoir containing a predetermined amount of hydraulic fluid, an implantable conduit providing fluid connection between said reservoir and said hydraulic adjustment device, an operation device adapted to be implanted in the patient for operating said hydraulic adjustment device by distributing hydraulic fluid through said conduit between said reservoir and said hydraulic adjustment device, and energy transfer means for transferring, directly or indirectly, wireless energy into an energy form suited for powering said operation device.

72. The apparatus according to claim 71, wherein said operation device is a hydraulic operation device and said conduit, hydraulic adjustment device and hydraulic operation device are devoid of any non-return valve to permit free flow of hydraulic fluid in both directions in said conduit.

73. The apparatus according to claim 72, wherein said operation device comprises a pump for distributing fluid in said conduit between said reservoir and said hydraulic adjustment device.

74. The apparatus according to claim 73, wherein said operation device comprises an electric motor for driving said pump.

75. The apparatus according to claim 71, further comprising a wireless remote control for controlling said restriction device.

76. The apparatus according to claim 71, wherein energy consuming implantable components of the apparatus are adapted to be energized with energy wirelessly transmitted from outside the patient's body.

77. The apparatus according to claim 71, further comprising a battery or accumulator adapted to be implanted in the patient for energizing energy consuming implantable components of the apparatus, wherein said battery or accumulator is adapted to be controlled from outside the patient's body to release energy.

78. An anal incontinence treatment apparatus, comprising:

an adjustable restriction device adapted to be implanted in a patient, who suffers from anal incontinence, to constrict the colon or rectum or the prolongation thereof to restrict the fecal passageway therein, an adjustment device adapted to be implanted in the patient for adjusting said restriction device to restrict the fecal passageway to prevent feces from passing therethrough and enlarge the fecal passageway to allow feces to readily pass therethrough, and energy transfer means for transferring, directly or indirectly, wireless energy into an energy form suited for powering said adjustment device, wherein said adjustment device comprises a servo device.

79. The apparatus according to claim 78, further comprising a powered operation device adapted to be implanted in the patient for operating said adjustment device.

80. The apparatus according to claim 78, wherein said servo device comprises a hydraulic operation device.

81. The apparatus according to claim 80, wherein said servo device comprises a servo reservoir defining a chamber containing servo fluid, and said hydraulic operation device comprises first and second wall portions of said servo reservoir, which are displaceable relative to each other to change the volume of said chamber of said servo reservoir.

82. The apparatus according to claim 81, wherein said first and second wall portions of said servo reservoir are displaceable relative to each other by manual manipulation.

83. The apparatus according to claim 81, wherein said first and second wall portions of said servo reservoir are displaceable relative to each other by a magnetic device, hydraulic device, or electric control device.

84. The apparatus according to claim 80, wherein said servo device comprises a servo reservoir and a fluid supply reservoir connected in a closed system and containing a predetermined amount of fluid.

85. The apparatus according to claim 84, wherein said fluid supply reservoir defines a chamber for the predetermined amount of fluid and said hydraulic operation device changes the volume of said chamber of said supply reservoir and thereby controls the amount of fluid in said servo reservoir.

86. The apparatus according to claim 85, wherein said fluid supply reservoir comprises first and second wall portions, which are displaceable relative to each other to change the volume of said chamber of said fluid supply reservoir.

87. The apparatus according to claim 86, wherein said fluid supply reservoir increases the amount of fluid in said servo reservoir in response to a predetermined first displacement of said first wall portion of said fluid supply reservoir relative to said second wall portion of said fluid supply reservoir and decreases the amount of fluid in said servo reservoir in response to a predetermined second displacement of said first wall portion of said fluid supply reservoir relative to said second wall portion of said fluid supply reservoir.

88. The apparatus according to claim 78, wherein said servo device comprises a magnetic device, or an electric device.

89. The apparatus according to claim 78, wherein said servo means comprises hydraulic device.

90. The apparatus according to claim 78, wherein said restriction device is non-inflatable.

91. An anal incontinence treatment apparatus, comprising:

an adjustable restriction device adapted to be implanted in a patient, who suffers from anal incontinence, to constrict the colon or rectum or the prolongation thereof to restrict the fecal passageway therein, an adjustment device adapted to be implanted in the patient for adjusting said restriction device to restrict the fecal passageway to prevent feces from passing therethrough and to enlarge the fecal passageway to allow feces to readily pass therethrough, and an energy transfer device adapted to be implanted in the patient for transferring wireless energy directly or indirectly into kinetic energy for energizing said adjustment device to adjust said restriction; device, wherein said operation device is devoid of operating permanent magnets.

92. The apparatus according to claim 91, further comprising a wireless remote control for controlling said restriction device.

93. The apparatus according to claim 91, wherein energy consuming implantable components of the apparatus are adapted to be energized with energy wirelessly transmitted from outside the patient's body.

94. The apparatus according to claim 91, further comprising a battery or accumulator adapted to be implanted in the patient for energizing energy consuming implantable components of the apparatus, wherein said battery or accumulator is adapted to be controlled from outside the patient's body to release energy.

95. An anal incontinence treatment apparatus, comprising:

an adjustable restriction device adapted to be implanted in a patient, who suffers from anal incontinence, to constrict the colon or rectum or the prolongation thereof to restrict the fecal passageway therein, an adjustment device adapted to be implanted in the patient for adjusting said restriction device to restrict the fecal passageway to prevent feces from passing therethrough and enlarge the fecal passageway to allow feces to readily pass therethrough, an electrically powered hydraulic operation device adapted to be implanted in the patient for operating said adjustment device, and an energy transfer means for transferring wireless energy into electric energy for powering said hydraulic operation device.

96. The apparatus according to claim 95, wherein said energy transfer means directly, during energy transfer, powers said hydraulic operation device with transferred electric energy.

97. The apparatus according to claim 95, wherein said energy transfer means transfers wireless energy in the form of a wave signal.

98. The apparatus according to claim 97, wherein said wave signal comprises an electromagnetic wave signal, a sound wave signal or a carrier wave signal for a remote control signal.

99. The apparatus according to claim 95, wherein said energy transfer means transfers wireless energy in the form of an electric field or a magnetic field.

100. The apparatus according to claim 95, further comprising a stabilizer adapted to be implanted in the patient for stabilizing the electric energy transferred by said energy transfer device.

101. The apparatus according to claim 100, wherein said stabilizer comprises a capacitor.

102. The apparatus according to claim 95, further comprising an electric motor adapted to be implanted in the patient for driving said hydraulic operation device.

103. The apparatus according to claim 95, wherein said hydraulic operation device comprises a pump.

104. An anal incontinence treatment apparatus, comprising:

an adjustable restriction device adapted to be implanted in a patient, who suffers from anal incontinence, to constrict the colon or rectum or the prolongation thereof to restrict the fecal passageway therein, an adjustment device adapted to be implanted in the patient for adjusting said restriction device to restrict the fecal passageway to prevent feces from passing therethrough and enlarge the fecal passageway to allow feces to readily pass therethrough, an operation device adapted to be implanted in the patient for operating said adjustment device, a wireless energy transmission device for transmitting sound energy, including ultrasonic or infrasonic energy, and energy transfer means for transferring, directly or indirectly, the transmitted sound energy into an energy form suited for powering said operation device.

105. The apparatus according to claim 104, wherein said operation device comprises a motor or pump.

106. The apparatus according to claim 104, further comprising an implantable accumulator or rechargeable battery, and an energy transfer device adapted to transfer said sound energy into electric energy for charging said accumulator or rechargeable battery.

107. A surgical method for treating anal incontinence, comprising:

implanting in the body of a patient suffering from anal incontinence an adjustable restriction device engaging the colon or rectum or the prolongation thereof to restrict the fecal passageway therein to prevent feces from passing therethrough, implanting an adjustment device for adjusting the restriction device, implanting an electrically powered hydraulic operation device for operating the adjustment device, transmitting wireless energy and transferring the wireless energy directly or indirectly into electric energy for powering the hydraulic operation device, and when desired to achieve defecation powering the hydraulic operation device with electric energy to operate the adjusting device to adjust the restriction device to temporarily enlarge the fecal passageway to allow feces to readily pass therethrough.

108. A surgical method as recited in claim 107, further comprising implanting an elongated restriction member of the restriction device around the colon or rectum or the prolongation thereof.

109. A surgical method as recited in claim 107, further comprising implanting the restriction device in the distal part of the rectum of the patient.

110. A surgical method as recited in claim 107, wherein the adjustment device comprises a servo means.

111. A surgical method as recited in claim 107, further comprising implanting an electric source of energy in the patient and providing a control device for controlling the source of energy from outside the patient's body to supply electric energy to the electrically powered hydraulic operation device.

112. A surgical method as recited in claim 107, comprising implanting in the body of the patient at least two adjustable restriction devices in engagement with the colon or rectum or the prolongation thereof to restrict the fecal passageway therein.

113. A laparoscopical surgical method for treating anal incontinence, comprising:

placing at least two laparoscopical trocars in a patient suffering from anal incontinence, inserting a dissecting tool through the trocars and dissecting an area of the colon or rectum or the prolongation thereof, implanting through the trocars an adjustable restriction device in engagement with the colon or rectum or the prolongation thereof to restrict the fecal passageway therein to prevent feces from passing therethrough, implanting a powered operation device in the patient for operating the restriction device, transmitting wireless energy and transferring the wireless energy into a form suited for powering the operation device, and when desired to achieve defecation adjusting the restriction device to temporarily enlarge the fecal passageway to allow feces to readily pass therethrough.

114. A surgical method as recited in claim 113, wherein said adjustment device is operated in a non-manual manner.

115. A surgical method as recited in claim 113, further comprising implanting a servo means for operating said restriction device.

116. A surgical method as recited in claim 113, further comprising implanting an electric source of energy in the patient and controlling the source of energy from outside the patient's body to supply electric energy to the electrically powered operation device.

117. A surgical method as recited in claim 113, wherein the operation device is electrically powered and further comprising transferring the wireless energy into electric energy.

118. A surgical method according to claim 113, further comprising implanting an internal control unit, and using the internal control unit to control the restriction device to change the restriction of the fecal passageway.

119. A method of treating a patient having anal incontinence disease, comprising:

(a) surgically implanting in the patient an operable restriction device engaging the patient's colon or rectum or the prolongation thereof to restrict the fecal passageway therein to prevent feces from passing therethrough, (b) implanting an internal energy source in the patient, (c) transmitting wireless energy from outside the patient's body, (d) transferring the wireless energy into storable energy and storing the storable energy in the internal source of energy, and (e) when desired to achieve defecation supplying energy from the internal energy source for operating the restriction device to temporarily enlarge the fecal passageway to allow feces to readily pass therethrough.

120. A surgical method according to claim 119, further comprising implanting an internal control unit, and using the internal control unit to control the restriction device to change the restriction of the fecal passageway.

121. A surgical method according to claim 119, further comprising implanting a motor or pump in the patient for operating the restriction device and controlling the motor or pump to operate the restriction device to change the restriction of the fecal passageway.

122. A laparoscopical surgical method for treating anal incontinence, comprising:

placing at least two laparoscopical trocars in a patient suffering from anal incontinence, inserting a dissecting tool through the trocars and dissecting an area of the colon or rectum or the prolongation thereof, implanting th rough the trocars an adjust able restriction device in engagement with the colon or rectum or the prolongation thereof to restrict the fecal passageway therein to prevent feces from passing therethrough, implanting an internal source of energy in the patient, transmitting wireless energy from outside the patient's body, transferring the wireless energy into storable energy and storing the storable energy in the internal source of energy, and when desired to achieve defecation supplying energy from the internal energy source for operating the restriction device to temporarily enlarge the fecal passageway to allow feces to readily pass therethrough.

123. A surgical method according to claim 122, further comprising implanting an internal control unit, and using the internal control unit to control the restriction device to change the restriction of the fecal passageway.

124. A surgical method according to claim 122, further comprising implanting a motor or pump in the patient for operating the restriction device and controlling the motor or pump to operate the restriction device to change the restriction of the fecal passageway.

125. A surgical method for treating anal incontinence, comprising:

implanting in the body of a patient suffering from anal incontinence an adjustable non-inflatable restriction device engaging the colon or rectum or the prolongation thereof to restrict the fecal passageway therein to prevent feces from passing therethrough, implanting an adjustment device for adjusting the restriction device, implanting an electrically powered operation device for operating the non-inflatable adjustment device, transmitting wireless energy and transferring the wireless energy into a form suited for powering, directly or indirectly, the operation device, and when desired to achieve defecation powering the operation device with electric energy to operate the adjusting device to adjust the restriction device to temporarily enlarge the fecal passageway to allow feces to readily pass therethrough.

126. A surgical method as recited in claim 125, further comprising implanting an elongated restriction member of the restriction device around the colon or rectum or the prolongation thereof.

127. A surgical method as recited in claim 125, further comprising implanting an electric source of energy in the patient and controlling the source of energy from outside the patient's body to supply electric energy to the electrically powered operation device.

* * * * *